US007165551B2

(12) United States Patent
Edwards et al.

(10) Patent No.: US 7,165,551 B2
(45) Date of Patent: *Jan. 23, 2007

(54) APPARATUS TO DETECT AND TREAT ABERRANT MYOELECTRIC ACTIVITY

(75) Inventors: Stuart D Edwards, Salinas, CA (US); David S Utley, Redwood City, CA (US); Ronald G Lax, Palm City, FL (US)

(73) Assignee: Curon Medical, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/924,935

(22) Filed: Aug. 8, 2001

(65) Prior Publication Data

US 2002/0143324 A1  Oct. 3, 2002

Related U.S. Application Data

(63) Continuation of application No. 09/026,085, filed on Feb. 19, 1998, now abandoned, and a continuation-in-part of application No. 09/360,599, filed on Jul. 26, 1999, now abandoned, which is a continuation of application No. 09/026,296, filed on Feb. 19, 1998, now Pat. No. 6,009,877.

(51) Int. Cl.
  *A61B 17/39* (2006.01)
  *A61B 18/18* (2006.01)
  *A61N 1/00* (2006.01)
(52) U.S. Cl. .................. 128/898; 606/41; 607/133
(58) Field of Classification Search .............. 606/41, 606/42, 45, 48–50; 607/100–102, 115, 116, 607/133
  See application file for complete search history.

(56) References Cited

U.S. PATENT DOCUMENTS

| 1,798,902 A | 3/1931 | Raney |
| 3,517,128 A | 6/1970 | Hines |
| 3,901,241 A | 8/1975 | Allen, Jr. |
| 4,011,872 A | 3/1977 | Komiya |
| 4,196,724 A | 4/1980 | Wirt et al. |
| 4,411,266 A | 10/1983 | Cosman |
| 4,423,812 A | 1/1984 | Sato |
| 4,532,924 A | 8/1985 | Auth et al. |
| 4,565,200 A | 1/1986 | Cosman |
| 4,705,041 A | 11/1987 | Kim |

(Continued)

FOREIGN PATENT DOCUMENTS

DE  43 03 882  2/1995

(Continued)

OTHER PUBLICATIONS

Karlstrom et al, "Ectompic jejunal . . . intestinal pacing", Surgery, 1989, 106(3):486-495.*

(Continued)

*Primary Examiner*—Michael Peffley
(74) *Attorney, Agent, or Firm*—Ryan Kromholz & Manion, S.C.

(57) ABSTRACT

An apparatus to treat a sphincter has a support member. A sphincter electropotential mapping device includes a mapping electrode. The sphincter electropotential mapping device is coupled to the support member and configured to detect aberrant myoelectric activity of the sphincter.

6 Claims, 29 Drawing Sheets

U.S. PATENT DOCUMENTS

| | | |
|---|---|---|
| 4,901,737 A | 2/1990 | Toone |
| 4,906,203 A | 3/1990 | Margrave et al. |
| 4,907,589 A | 3/1990 | Cosman |
| 4,943,290 A | 7/1990 | Rexroth et al. |
| 4,947,842 A | 8/1990 | Marchosky et al. |
| 4,955,377 A | 9/1990 | Lennox et al. |
| 4,966,597 A | 10/1990 | Cosman |
| 4,976,711 A | 12/1990 | Parins et al. |
| 5,019,075 A | 5/1991 | Spears et al. |
| 5,035,696 A | 7/1991 | Rydell |
| 5,046,512 A | 9/1991 | Murchie |
| 5,047,028 A | 9/1991 | Qian |
| 5,057,107 A | 10/1991 | Parins et al. |
| 5,078,717 A | 1/1992 | Parins et al. |
| 5,083,565 A | 1/1992 | Parins |
| 5,084,044 A | 1/1992 | Quint |
| 5,088,979 A | 2/1992 | Filipi et al. |
| 5,094,233 A | 3/1992 | Brennan |
| 5,100,423 A | 3/1992 | Fearnot |
| 5,106,360 A | 4/1992 | Ishiwara et al. |
| 5,122,137 A | 6/1992 | Lennox |
| 5,125,928 A | 6/1992 | Parins et al. |
| 5,156,151 A * | 10/1992 | Imran .................... 600/375 |
| 5,190,541 A | 3/1993 | Abele et al. |
| 5,197,963 A | 3/1993 | Parins |
| 5,197,964 A | 3/1993 | Parins |
| 5,205,287 A | 4/1993 | Erbel et al. |
| 5,215,103 A | 6/1993 | Desai |
| 5,228,442 A | 7/1993 | Imran |
| 5,232,444 A | 8/1993 | Just et al. |
| 5,236,413 A | 8/1993 | Fiering |
| 5,242,441 A | 9/1993 | Avitall |
| 5,254,126 A | 10/1993 | Filipi et al. |
| 5,256,138 A | 10/1993 | Vurek et al. |
| 5,257,451 A | 11/1993 | Edwards et al. |
| 5,263,493 A * | 11/1993 | Avitall .................... 600/374 |
| 5,275,162 A | 1/1994 | Edwards et al. |
| 5,275,608 A | 1/1994 | Forman et al. |
| 5,275,610 A | 1/1994 | Eberbach |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,292,321 A | 3/1994 | Lee |
| 5,293,869 A | 3/1994 | Edwards et al. |
| 5,309,910 A | 5/1994 | Edwards et al. |
| 5,313,943 A | 5/1994 | Houser et al. |
| 5,314,466 A | 5/1994 | Stern et al. |
| 5,316,020 A | 5/1994 | Truffer |
| 5,324,284 A | 6/1994 | Imran |
| 5,328,467 A | 7/1994 | Edwards et al. |
| 5,334,196 A | 8/1994 | Scott et al. |
| 5,336,222 A | 8/1994 | Durgin, Jr. et al. |
| 5,345,936 A | 9/1994 | Pomeranz et al. |
| 5,348,554 A | 9/1994 | Imran et al. |
| 5,363,861 A | 11/1994 | Edwards et al. |
| 5,365,926 A | 11/1994 | Desai |
| 5,365,945 A | 11/1994 | Halstrom |
| 5,366,490 A | 11/1994 | Edwards et al. |
| 5,368,557 A | 11/1994 | Nita et al. |
| 5,368,592 A | 11/1994 | Stern et al. |
| 5,370,675 A | 12/1994 | Edwards et al. |
| 5,370,678 A | 12/1994 | Edwards et al. |
| 5,383,876 A | 1/1995 | Nardella |
| 5,383,917 A | 1/1995 | Desai et al. |
| 5,385,544 A | 1/1995 | Edwards et al. |
| 5,397,339 A | 3/1995 | Desai |
| 5,398,683 A | 3/1995 | Edwards et al. |
| 5,400,783 A | 3/1995 | Pomeranz et al. |
| 5,401,272 A | 3/1995 | Perkins |
| 5,403,311 A * | 4/1995 | Abele et al. .................... 604/21 |
| 5,409,000 A | 4/1995 | Imran |
| 5,409,453 A | 4/1995 | Lundquist et al. |
| 5,409,483 A | 4/1995 | Campbell et al. |
| 5,415,657 A | 5/1995 | Taymor-Luia |
| 5,421,819 A | 6/1995 | Edwards et al. |
| 5,423,808 A | 6/1995 | Edwards et al. |
| 5,423,811 A | 6/1995 | Ellman et al. |
| 5,423,812 A | 6/1995 | Ellman et al. |
| 5,433,739 A | 7/1995 | Sluijter et al. |
| 5,435,805 A | 7/1995 | Edwards |
| 5,441,499 A | 8/1995 | Fritzsch |
| 5,443,470 A | 8/1995 | Stern et al. |
| 5,454,782 A | 10/1995 | Perkins |
| 5,456,662 A | 10/1995 | Edwards et al. |
| 5,456,682 A | 10/1995 | Edwards et al. |
| 5,458,596 A | 10/1995 | Lax et al. |
| 5,458,597 A | 10/1995 | Edwards et al. |
| 5,465,717 A | 11/1995 | Imran et al. |
| 5,470,308 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,485,849 A | 1/1996 | Panescu et al. |
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,500,012 A | 3/1996 | Brucker et al. |
| 5,505,728 A | 4/1996 | Ellman et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,520,684 A | 5/1996 | Imran |
| 5,531,676 A | 7/1996 | Edwards et al. |
| 5,531,677 A | 7/1996 | Lundquist et al. |
| 5,536,240 A | 7/1996 | Edwards et al. |
| 5,536,267 A | 7/1996 | Edwards et al. |
| 5,540,655 A | 7/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,571,116 A | 11/1996 | Bolanos et al. |
| 5,578,007 A | 11/1996 | Imran |
| 5,588,432 A | 12/1996 | Crowley |
| 5,588,960 A | 12/1996 | Edwards et al. |
| 5,595,183 A | 1/1997 | Swanson et al. |
| 5,599,345 A | 2/1997 | Edwards et al. |
| 5,609,151 A | 3/1997 | Mulier et al. |
| 5,624,439 A | 4/1997 | Edwards et al. |
| 5,672,153 A | 9/1997 | Lax et al. |
| 5,676,674 A | 10/1997 | Bolanos et al. |
| 5,688,266 A | 11/1997 | Edwards et al. .............. 606/31 |
| 5,688,490 A | 11/1997 | Tournier et al. |
| 5,702,438 A | 12/1997 | Avitall |
| 5,709,224 A | 1/1998 | Behl et al. |
| 5,732,698 A | 3/1998 | Swanson et al. |
| 5,738,096 A | 4/1998 | Ben-Haim |
| 5,823,197 A * | 10/1998 | Edwards .................... 128/898 |
| 5,830,213 A | 11/1998 | Panescu et al. |
| 5,836,874 A | 11/1998 | Swanson et al. |
| 5,860,974 A | 1/1999 | Abele |
| 5,871,483 A | 2/1999 | Jackson et al. |
| 6,006,755 A | 12/1999 | Edwards |
| 6,009,877 A | 1/2000 | Edwards |
| 6,044,846 A | 4/2000 | Edwards |
| 6,056,744 A | 4/2000 | Edwards |
| 6,073,052 A | 6/2000 | Zelickson et al. |

| | | | |
|---|---|---|---|
| 6,077,257 A * | 6/2000 | Edwards et al. | 604/506 |
| 6,092,528 A | 7/2000 | Edwards | |
| 6,156,032 A | 12/2000 | Lennox | |
| 6,197,022 B1 | 3/2001 | Baker | |
| 6,254,598 B1 * | 7/2001 | Edwards et al. | 606/41 |
| 6,258,087 B1 * | 7/2001 | Edwards et al. | 606/41 |
| 6,402,744 B1 * | 6/2002 | Edwards et al. | 606/41 |
| 6,405,732 B1 | 6/2002 | Edwards et al. | |
| 6,589,238 B1 | 7/2003 | Edwards et al. | |

FOREIGN PATENT DOCUMENTS

| | | |
|---|---|---|
| DE | 38 38 840 | 2/1997 |
| EP | 0 139 607 | 5/1985 |
| EP | 0 608 609 | 8/1994 |
| WO | 91/01773 | 2/1991 |
| WO | 92/10142 | 6/1992 |
| WO | 93/08755 | 5/1993 |
| WO | 94/10925 | 5/1994 |
| WO | 94/21165 | 9/1994 |
| WO | 94/21178 | 9/1994 |
| WO | 94/22366 | 10/1994 |
| WO | WO 94/22366 | 10/1994 |
| WO | 94/26178 | 11/1994 |
| WO | 95/18575 | 7/1995 |
| WO | 95/19142 | 7/1995 |
| WO | 95/25472 | 9/1995 |
| WO | 96/00042 | 1/1996 |
| WO | 96/16606 | 6/1996 |
| WO | 96/29946 | 10/1996 |
| WO | 97/06857 | 2/1997 |
| WO | 97/32532 | 9/1997 |
| WO | 97/43971 | 11/1997 |

OTHER PUBLICATIONS

Castell, D.O. "Gastroesophageal Reflux Disease: Current Strategies for Patient Management." Arch Fam Med. 5(4): 221-7.

Dallemagne, B. et al., "Laparoscopic Nissen Fundoplication: Preliminary." Surgical Laparoscopy & Endoscopy. 1991 1(3): 138-43.

Kelly, KA. et al., "Doudenal-gastric reflux and slowed gastric emptying by electrical pacing of the canine duodenal pacesetter potential." Gastroenterology. 1977. 72(3): 429-33.

Reynolds, J.C. "Influence of pathophysiology, severity, and cost on the medical management of gastroesophageal reflux disease." Am J Health-Syst Pharm. 53 (22 Suppl 3): S5-12.

Urschel, J.D. "Complications of Antireflux Surgery." Am J Surg. 1993. 166(1): 68-70.

Kaneko, et al., Physiological Laryngeal Pacemaker, May 1985, Trans Am Soc. Artif. Intern Organs, vol. XXXI, pp. 293-296.

Mugica et al. Direct Diaphragm Stimulation, Jan. 1987 PACE, vol. 10, pp. 252-256.

Mugica et al., Neurostimulation: An Overview, Chapter 21, Preliminary Test of a Muscular Diaphragm pacing System on Human Patients. 1985. pgs3. 263-279.

Rice et al., Endoscopic Paranasal Sinus Surgery, Chapter 5, Functional Endoscopic Paranasal Sinus Surgery, The Technique of Messerklinger, Raven Press, 1988, pp. 75-104.

Rice et al., Endoscopic Paranasal Sinus Surgery, Chapter 6, Total Endoscopic Sphenoethmoidectomy, The Technique of Wigand, Raven Press, 1988, pp. 105-125.

Hinder, R.A. et al., "The Technique of Laparoscopic Nissen Fundoplication." Surgical Laparoscopy & Endoscopy. 1992. 2(3): 265-272.

Karistrom, L.H. et al. "Ectopic jejunal pacemakers and enterogastric reflux after Roux gastrectomy: Effect of intestinal pacing." Surgery 1989. 106(3): 486-495.

* cited by examiner

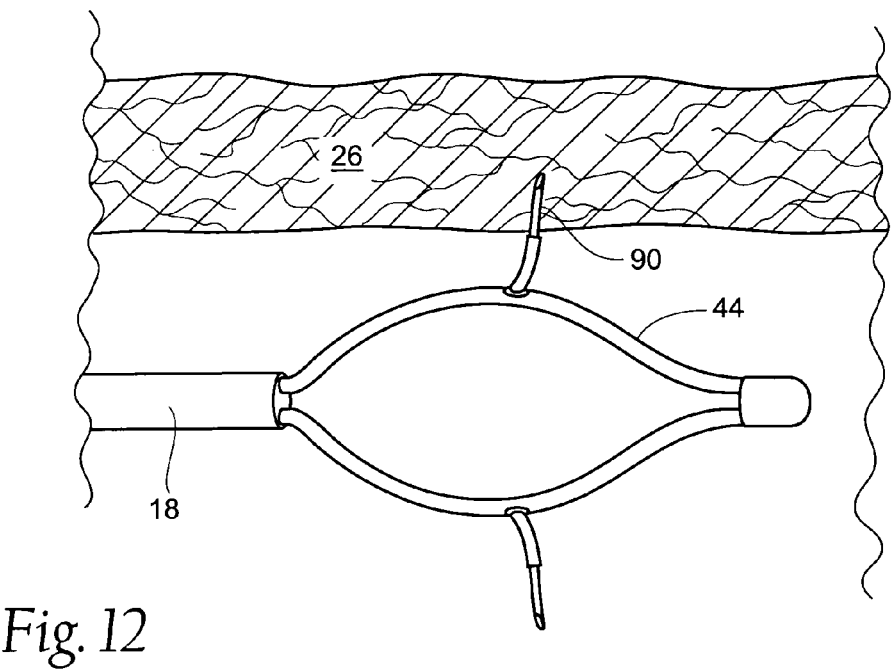
Fig. 12
Fig. 13
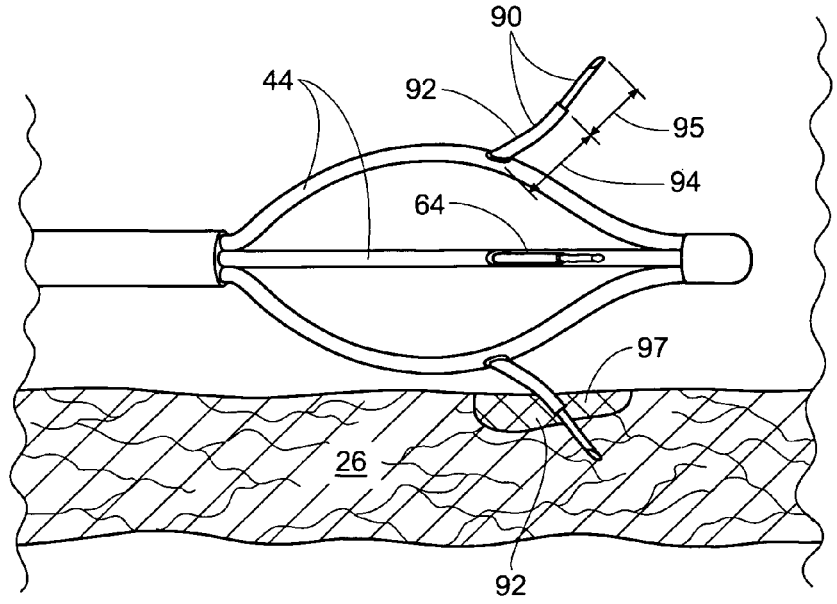

APPARATUS TO DETECT AND TREAT ABERRANT MYOELECTRIC ACTIVITY

CROSS-RELATED APPLICATIONS

This application is a continuation of U.S. patent application Ser. No. 09/026,085, filed Feb. 19, 1998, now abandoned. This application is also a continuation-in-part of U.S. patent application Ser. No. 09/360,599, filed Jul. 26, 1999, now abandoned, which is a continuation of U.S. Patent Application Ser. No. 09/026,296, filed Feb. 19, 1998, now U.S. Pat. No. 6,009,877.

BACKGROUND OF THE INVENTION

1. Field of the Invention

This invention relates generally to an apparatus to detect and treat aberrant myoelectric activity, and more particularly the detection and treatment in a sphincter and/or stomach.

2. Description of Related Art

Gastroesophageal reflux disease (GERD) is a common gastroesophageal disorder in which the stomach contents are ejected into the lower esophagus due to a dysfunction of the lower esophageal sphincter (LES). These contents are highly acidic and potentially injurious to the esophagus resulting in a number of possible complications of varying medical severity. The reported incidence of GERD in the U.S. is as high as 10% of the population (Castell D O; Johnston B T: *Gastroesophageal Reflux Disease: Current Strategies For Patient Management*. Arch Fam Med, 5(4):221–7; (1996 April)).

Acute symptoms of GERD include heartburn, pulmonary disorders and chest pain. On a chronic basis, GERD subjects the esophagus to ulcer formation, or esophagitis and may result in more severe complications including esophageal obstruction, significant blood loss and perforation of the esophagus. Severe esophageal ulcerations occur in 20–30% of patients over age 65. Moreover, GERD causes adenocarcinoma, or cancer of the esophagus, which is increasing in incidence faster than any other cancer (Reynolds J C: *Influence Of Pathophysiology, Severity, And Cost On The Medical Management Of Gastroesophageal Reflux Disease*. Am J Health Syst Pharm, 53(22 Suppl 3):S5–12 (Nov. 15, 1996)).

One of the possible causes of GERD may be aberrant electrical signals in the LES or the stomach. Such signals may cause a higher than normal frequency of relaxations of the LES allowing acidic stomach contents to be repeatedly ejected into the esophagus and cause the complications described above. Research has shown that unnatural electrical signals in the stomach and intestine can cause reflux events in those organs (Kelly K A, et al: *Duodenal-gastric Reflux and Slowed Gastric Emptying by Electrical Pacing of the Canine Duodenal Pacesetter Potential*. Gastroenterology. 1977 March; 72(3):429–433). In particular, medical research has found that sites of aberrant electrical activity or electrical foci may be responsible for those signals (Karlstrom L H, et al.: *Ectopic Jejunal Pacemakers and Enterogastric Reflux after Roux Gastrectomy: Effect Intestinal Pacing*. Surgery. 1989 September; 106(3):486–495). Similar aberrant electrical sites in the heart, which cause contractions of the heart muscle to take on life threatening patterns or dysrhythmias, can be identified and treated using mapping and ablation devices as described in U.S. Pat. No. 5,509,419. However, there is no current device or associated medical procedure available for the electrical mapping and treatment of aberrant electrical sites in the LES and stomach as a means for treating GERD.

Current drug therapy for GERD includes histamine receptor blockers which reduce stomach acid secretion and other drugs which may completely block stomach acid. However, while pharmacologic agents may provide short term relief, they do not address the underlying cause of LES dysfunction.

Invasive procedures requiring percutaneous introduction of instrumentation into the abdomen exist for the surgical correction of GERD. One such procedure, Nissen findoplication, involves constructing a new "valve" to support the LES by wrapping the gastric fundus around the lower esophagus. Although the operation has a high rate of success, it is an open abdominal procedure with the usual risks of abdominal surgery including: postoperative infection, herniation at the operative site, internal hemorrhage and perforation of the esophagus or of the cardia. In fact, a recent 10 year, 344 patient study reported the morbidity rate for this procedure to be 17% and mortality 1% (Urschel, J D: *Complications Of Antireflux Surgery*, Am J Surg 166(1): 68–70; (1993 July)). This rate of complication drives up both the medical cost and convalescence period for the procedure and may exclude portions of certain patient populations (e.g., the elderly and immuno-compromised).

Efforts to perform Nissen fundoplication by less invasive techniques have resulted in the development of laparoscopic Nissen fundoplication. Laparoscopic Nissen fundoplication, reported by Dallemagne et al. *Surgical Laparoscopy and Endoscopy*, Vol. 1, No. 3, (1991), pp. 138–43 and by Hindler et al. *Surgical Laparoscopy and Endoscopy*, Vol. 2, No. 3, (1992), pp. 265–272, involves essentially the same steps as Nissen findoplication with the exception that surgical manipulation is performed through a plurality of surgical cannula introduced using trocars inserted at various positions in the abdomen.

Another attempt to perform findoplication by a less invasive technique is reported in U.S. Pat. No. 5,088,979. In this procedure an invagination device containing a plurality of needles is inserted transorally into the esophagus with the needles in a retracted position. The needles are extended to engage the esophagus and fold the attached esophagus beyond the gastroesophageal junction. A remotely operated stapling device, introduced percutaneously through an operating channel in the stomach wall, is actuated to fasten the invaginated gastroesophageal junction to the surrounding involuted stomach wall.

Yet another attempt to perform fundoplication by a less invasive technique is reported in U.S. Pat. No. 5,676,674. In this procedure, invagination is done by a jaw-like device and fastening of the invaginated gastroesophageal junction to the fundus of the stomach is done via a transoral approach using a remotely operated fastening device, eliminating the need for an abdominal incision. However, this procedure is still traumatic to the LES and presents the postoperative risks of gastroesophageal leaks, infection and foreign body reaction, the latter two sequela resulting when foreign materials such as surgical staples are implanted in the body.

While the methods reported above are less invasive than an open Nissen fundoplication, some still involve making an incision into the abdomen and hence the increased morbidity and mortality risks and convalescence period associated with abdominal surgery. Others incur the increased risk of infection associated with placing foreign materials into the body. All involve trauma to the LES and the risk of leaks developing at the newly created gastroesophageal junction.

None provide a means for detecting and treating aberrant electrical sites causing abnormal LES relaxation and gastroesophageal reflux.

There is a need to provide an apparatus to detect and treat aberrant myoelectric activity of a sphincter and/or a stomach. There is another need to provide an apparatus to detect and treat an electrical foci of the aberrant myoelectric activity of a sphincter and/or a stomach. There is a further need to detect and treat an electrically conductive pathway of the aberrant myoelectric activity of a sphincter and/or a stomach.

SUMMARY OF THE INVENTION

Accordingly, an object of the invention is to provide an apparatus to diagnose and treat sphincters and/or a stomach.

Another object of the invention is to provide an apparatus to diagnose and treat GERD.

A further object of the invention is to provide an apparatus to detect and treat aberrant myoelectric activity of a sphincter and/or a stomach.

Yet another object of the invention is to provide an apparatus to detect and treat an electrical foci of aberrant myoelectric activity of a sphincter and/or a stomach.

Still a further object of the invention is to provide an apparatus to detect and treat an electrically conductive pathway of aberrant myoelectric activity of a sphincter and/or a stomach.

Another object of the invention is to provide an apparatus to detect and treat an electrical foci of aberrant myoelectric activity of a lower esophageal sphincter and/or a stomach.

A further object of the invention is to provide an apparatus to detect and treat an electrically conductive pathway of aberrant myoelectric activity of a lower esophageal sphincter and/or a stomach.

These and other objects of the invention are provided in an apparatus to treat a sphincter that has a support member. A sphincter electropotential mapping device includes a mapping electrode. The sphincter electropotential mapping device is coupled to the support member and configured to detect one of an aberrant neuroelectric or myoelectric activity of the sphincter or stomach.

In another embodiment, an apparatus to treat a stomach has a support member. A stomach electropotential mapping device includes a mapping electrode. The stomach electropotential mapping device is coupled to the support member and configured to detect and treat one of an aberrant neuroelectric or myoelectric activity of the stomach.

Additionally, the electropotential mapping device can also include one or more treatment electrodes.

BRIEF DESCRIPTION OF THE DRAWINGS

FIG. 12 is a lateral view of the basket assembly illustrating the use of needle electrodes.

FIG. 13 is a lateral view illustrating the use of an insulation segment on the needle electrode to protect an area of tissue from RF energy.

DETAILED DESCRIPTION

Figure 1:
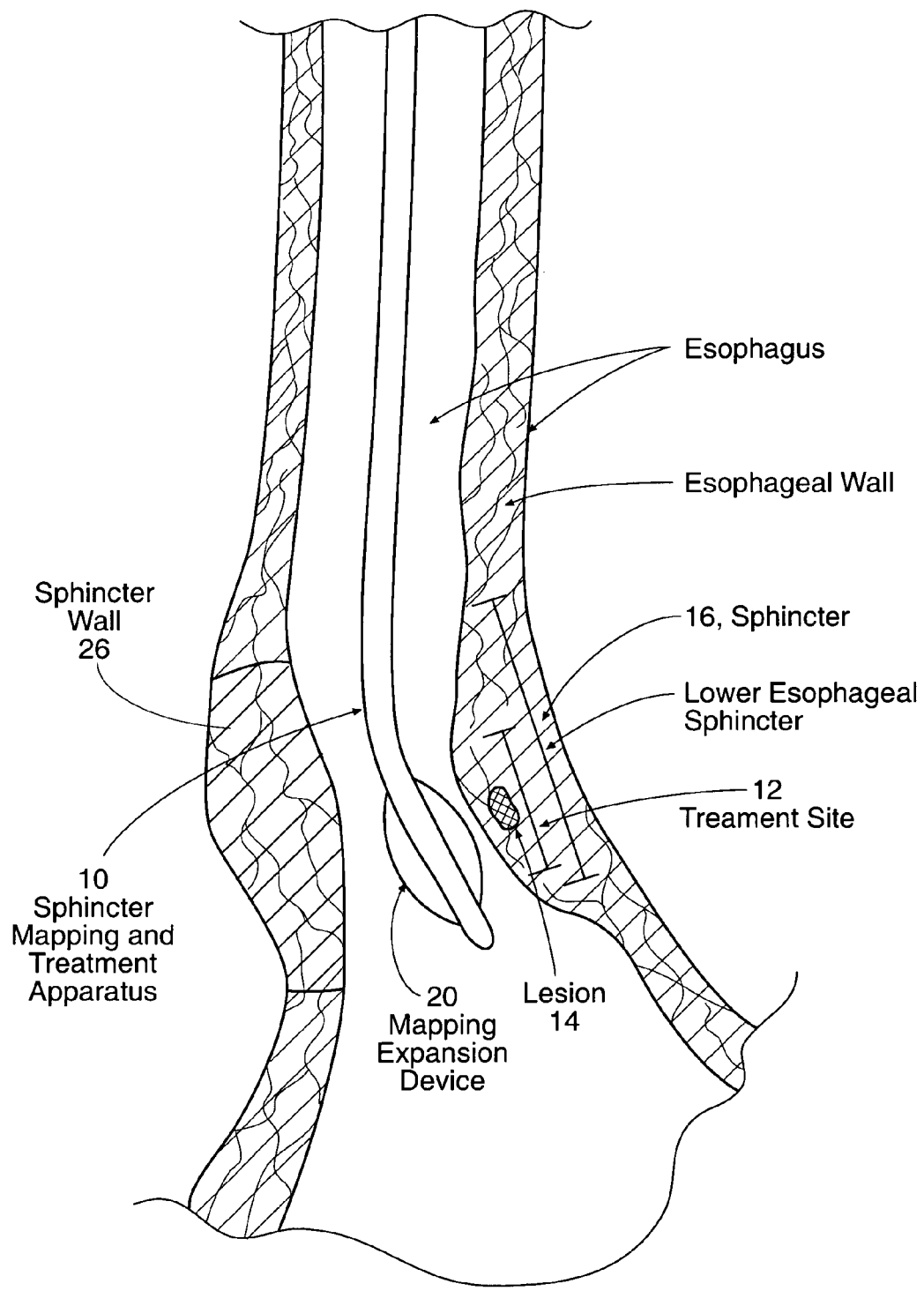
FIG. 1 is an illustrated lateral view of the upper GI tract including the esophagus and lower esophageal sphincter and the positioning of the sphincter mapping and treatment apparatus of the present invention in the lower esophageal sphincter.
Figure 2:
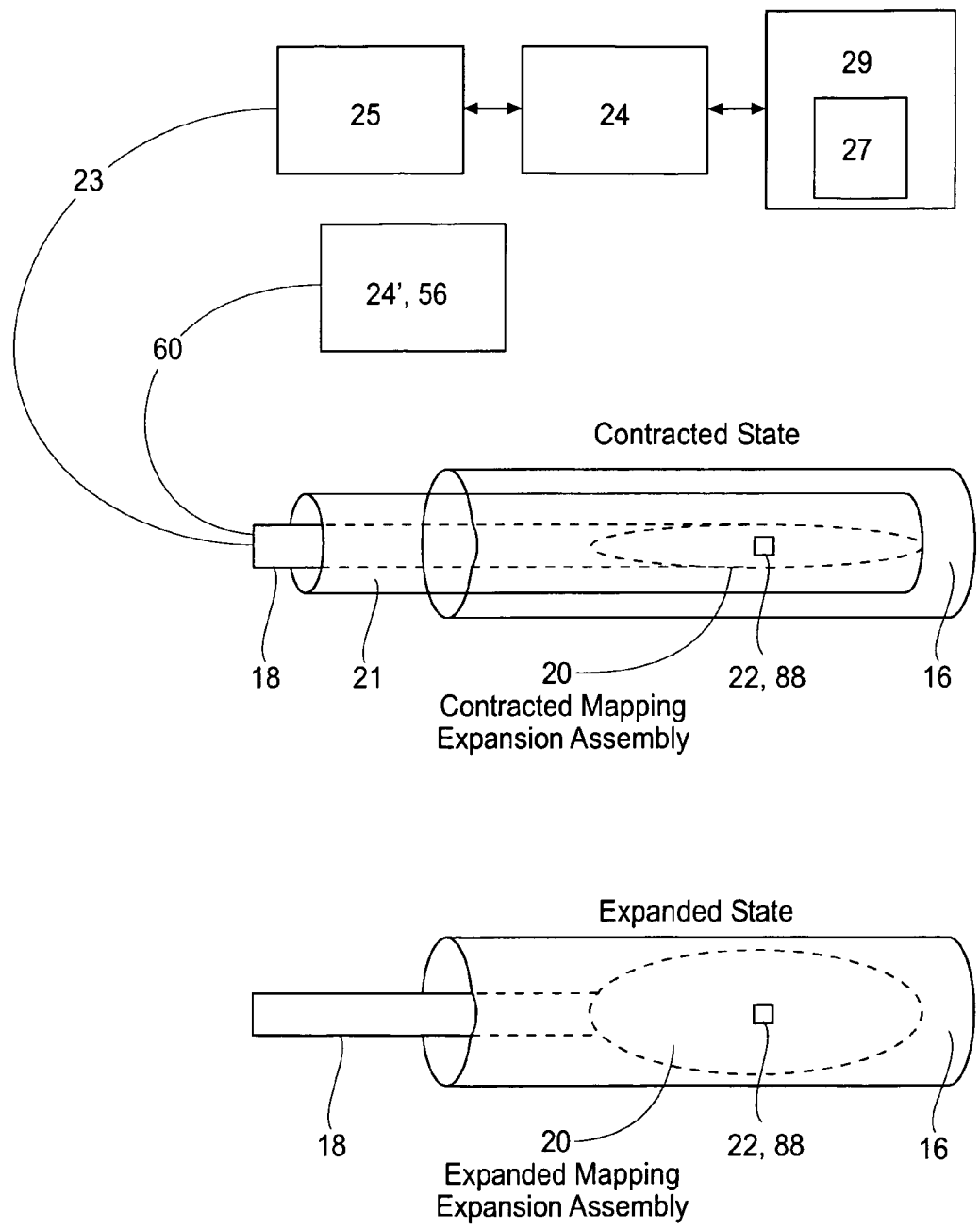
FIG. 2 is a lateral view of the present invention illustrating the energy delivery device, power source, controllers, map, display device, and the mapping assembly in an expanded and contracted state.

Referring now to FIGS. 1 and 2, one embodiment of sphincter mapping and treatment apparatus 10 that is used to map the myoelectric activity of and deliver energy to a treatment site 12 to produce lesions 14 in a sphincter 16, such as the lower esophageal sphincter (LES), comprises a flexible elongate shaft 18, also called shaft 18, coupled to an expandable mapping assembly 20, in turn coupled with one or more mapping electrodes 22.

Expandable mapping assembly 20 establishes a three dimensional array of mapping electrodes 22. In use, the expandable mapping assembly 20 records the activation times, the distribution, and the waveforms of the myoelectrical and neuroelectrical action potentials in sphincter 16, which can include the LES, and adjoining structures that trigger aberrant relaxation of muscle tissue in sphincter 16. Suitable materials for mapping electrodes 22 include gold, platinum and other metals known to those skilled in the art.

Mapping electrodes 22 are configured to be coupled to a controller 24. Controller 24 receives and processes the potentials recorded by the mapping electrodes 22 on expandable mapping assembly 20 and produces an electropotential map 27, also called a map, of the myoelectric and neuroelectric activity in sphincter 16. Controller 24 and electropotential map 27 are used by the physician to diagnose abnormalities and pathologies within sphincter 16 and adjoining structures which will be further discussed herein. Controller 24 can be coupled to an output or display device 29 that can include a cathode ray tube, liquid crystal display, passive or active matrix flat screen display or printer and the like.

Expandable mapping assembly 20 has a central longitudinal axis 28 and is moveable between contracted and expanded positions substantially there along. This can be accomplished by a ratchet mechanism as is known to those skilled in the art and by the use of other mechanisms disclosed herein. The expandable mapping assembly 20 is further configured to be positionable in a sphincter 16 such as the LES or adjacent anatomical structure, such as the cardia of the stomach. Once positioned within the desired sphincter 16, the operating physician causes expandable mapping assembly 20 to expand to an expanded stationary position within the sphincter so that mapping electrodes 22 thereof engage sphincter wall 26 for sensing and detecting electrical energy or impulses therefrom. At least portions of sphincter mapping and treatment apparatus 10 may be sufficiently radiopaque in order to be visible under fluoroscopy and/or sufficiently echogenic to be visible under ultrasonography. Also, as will be discussed herein, sphincter mapping and treatment apparatus 10 can include visualization capability including, but not limited to, a viewing scope, an expanded eyepiece, fiber optics, video imaging and the like.

Referring to FIG. 2, shaft 18 is configured to be coupled to expandable mapping assembly 20 and has sufficient length to position expandable mapping assembly 20 in the LES and/or stomach using a transoral approach. Typical lengths for shaft 18 include, but are not limited to, a range of 40–180 cm. In various embodiments, shaft 18 is flexible, articulated and steerable and can contain fiber optics (including illumination and imaging fibers), fluid and gas paths, and sensor and electronic cabling. In one embodiment, shaft 18 can be a multi-lumen catheter, as is well known to those skilled in the art.

In another embodiment of the invention, an introducing member 21, also called an introducer, is used to introduce sphincter mapping and treatment apparatus 10 into the LES. Introducer 21 can also function as a sheath for expandable mapping assembly 20 to keep it in a nondeployed or contracted state during introduction into the LES. In various embodiments, introducer 21 is flexible, articulated and steerable, and contains a continuous lumen of sufficient diameter to allow the advancement of sphincter mapping and treatment apparatus 10 within. Typical diameters for introducer 21 include 0.1 to 2 inches, while typical length include 40–180 cm. Suitable materials for introducer 21 include wire-reinforced plastic tubing as is well known to those skilled in the art.

Figure 3:
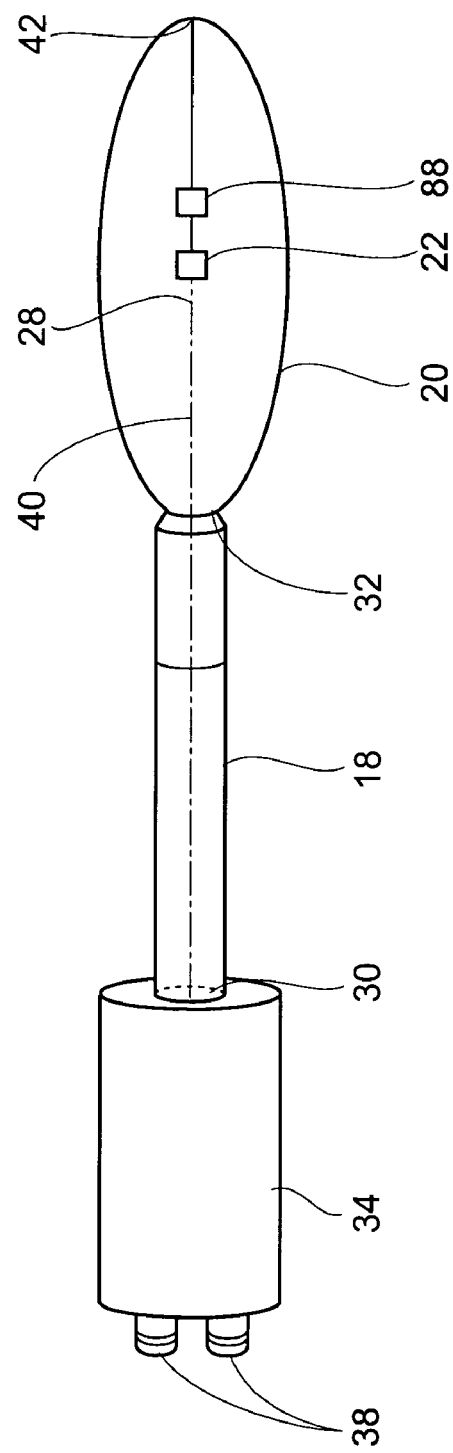
FIG. 3 depicts a lateral view of the present invention that illustrates components on the flexible shaft including a proximal fitting, connections and proximal and distal shaft segments.

Referring now to FIG. 3, the flexible elongate shaft 18 is circular in cross section and has proximal and distal extremities (also called ends) 30 and 32. Shaft 18 may also be coupled at its proximal end 32 to a proximal fitting 34, also-called a handle, used by the physician to manipulate sphincter mapping and treatment apparatus 10 to reach treatment site 12. Shaft 18 may have one or more shaft lumens 36, that extend the full length of shaft 18, or part way from shaft proximal end 30 to shaft distal end 32. Shaft lumens 36 may be used as paths for catheters, guide wires, pull wires, insulated wires and cabling, fluid and optical fibers. Shaft lumens 36 are connected to and/or accessed by connections 38, also called connector 38, on or adjacent to proximal fitting 34. Connections 38 can include luer-lock, swage and other mechanical varieties well known to those skilled in the art. Connections 38 can also include electrical connections 38' which can include lemo connectors, micro connectors and other electrical varieties well known to those skilled in the art. Additionally, connectors 38 can include opto-electronic connections 38" which allow optical and electronic coupling of optical fibers and/or viewing scopes to illuminating sources, eye pieces and video monitors. In various embodiments, shaft 18 may stop at the proximal extremity 40 of expandable mapping assembly 20 or extend to, or past, the distal extremity 42 of expandable mapping assembly 20. Suitable materials for shaft 18 include, but are not limited to, polyethylenes, polyurethanes and other medical plastics known to those skilled in the art.

Figure 4A:
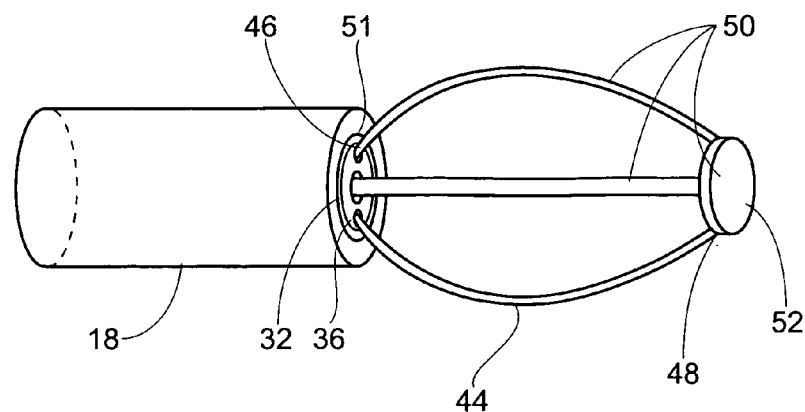
FIG. 4A illustrates a lateral view of the basket assembly used in an embodiment of the invention.

Referring now to FIG. 4, in one embodiment of the present invention, expandable mapping assembly 20 comprises one or more elongated arms 44 that are joined at their proximal arm ends 46 and distal arm ends 48 to form a basket assembly 50. Proximal arm end 46 is attached to a supporting structure, which can be the distal end 32 of shaft 18 or a proximal cap 51. Likewise, distal arm end 48 is also attached to a supporting structure which can be a distal basket cap 52 or shaft 18. Attached arms 44 may form a variety of geometric shapes including, but not limited to, curved, rectangular, trapezoidal and triangular. Arms 44 can have a variety of cross sectional geometries including, but not limited to, circular, rectangular and crescent-shaped. Also, arms 44 are of a sufficient number (two or more), and have sufficient spring force (0.01 to 0.5 lbs. force) so as to collectively exert adequate force on sphincter wall 26 to sufficiently open and efface the folds of sphincter 16 to allow treatment with sphincter mapping and treatment apparatus 10, while preventing herniation of sphincter wall 26 into the spaces 53 between arms 44. Suitable materials for arms 44 include, but are not limited to, spring steel, stainless steel, superelastic shape memory metals such as nitinol or wire-reinforced plastic tubing as is well known to those skilled in the art.

Figure 4B:
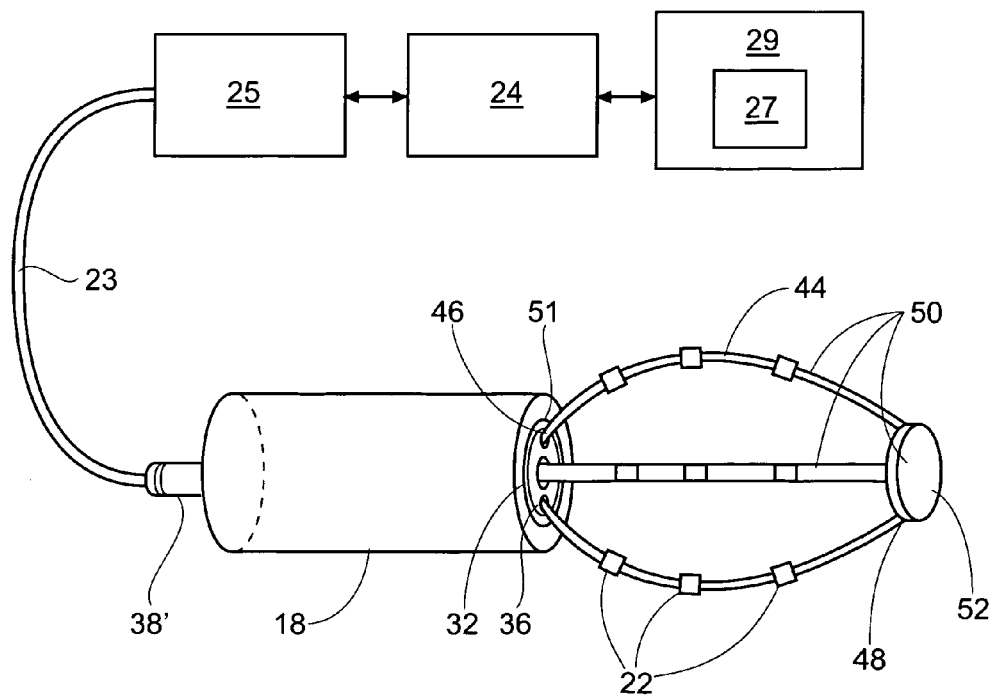
FIG. 4B is a lateral view that illustrates placement of the mapping electrodes on the basket assembly and their electrical connections to the controller.

Referring now to FIG. 4B, a plurality of spaced apart mapping electrodes 22 are carried by each arm 44 for engaging sphincter wall 26 and are electrically coupled by a conductor 23 to a multiplexer chip 25 for transmitting signals sensed thereby to controller 24 via electrical connections 38'. Various geometric patterns for placement of mapping electrodes 22 on basket assembly 50 or expandable mapping assembly 20 are disclosed later herein. Multiplexor chip 25 transmits only a selected one of the electrode signals at a time to the controller 24, subject to switching signals that controller 24 generates. The switching signals of controller 24 serve to multiplex the electrode signals through electrical connector 38'. This reduces the number of electrical pathways required through shaft lumen 36. In various embodiments, conductor 23 can be an insulated lead wire as is well known to those skilled in the art.

In various embodiments, expandable mapping assembly 20 or basket assembly 50 may also be coupled to one or more energy delivery devices 88, also called electrodes, coupled to power source 56. Energy delivery devices 88 are used to delivery energy to treatment site 12 to produce lesions 14. Expandable mapping assembly 20 is further configured to facilitate the positioning of energy delivery devices 88, to a selectable depth in a sphincter wall 26 or adjoining anatomical structure. In one embodiment mapping electrodes 22 can also be used as energy delivery devices.

Figure 5A:
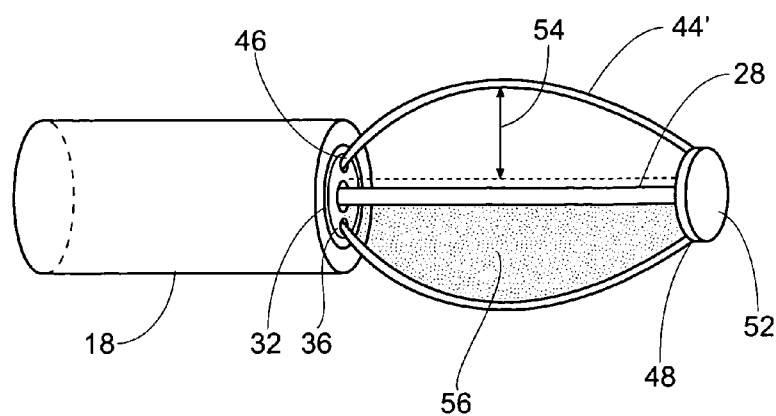
FIG. 5A is a lateral view of the basket assembly that illustrates the range of camber in the basket assembly.

Referring to FIG. 5A, arms 44 can have an outwardly bowed shaped memory for expanding the basket assembly into engagement with sphincter wall 26 with the amount of bowing, or camber 54 being selectable from a range 0 to 2 inches from longitudinal axis 28 of basket assembly 50. For the case of a curve-shaped arm 44', expanded arms 44' are circumferentially and symmetrically spaced-apart.

Figure 5B:
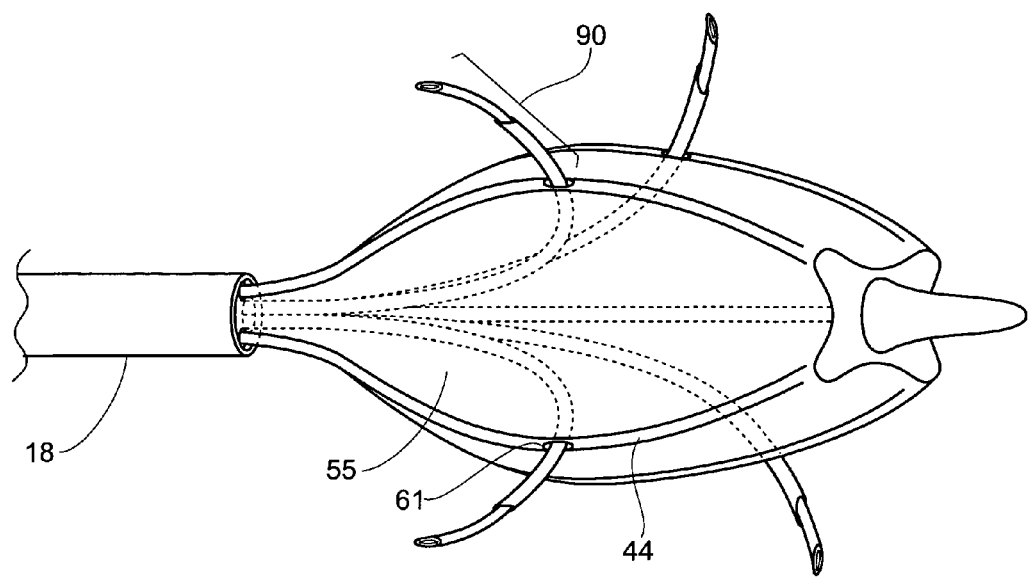
FIG. 5B is a perspective view illustrating a balloon coupled to the basket assembly.

In another embodiment shown in FIG. 5B, an expansion device 55, which can be a balloon, is coupled to an interior or exterior of basket assembly 50. Balloon 55 is also coupled to and inflated by shaft lumen 36 using gas or liquid. In various other embodiments (not shown), arms 44 may be asymmetrically spaced and/or distributed on an arc less than 360°. Also, arms 44 may be preshaped at time of manufacture or shaped by the physician.

Figure 6A:
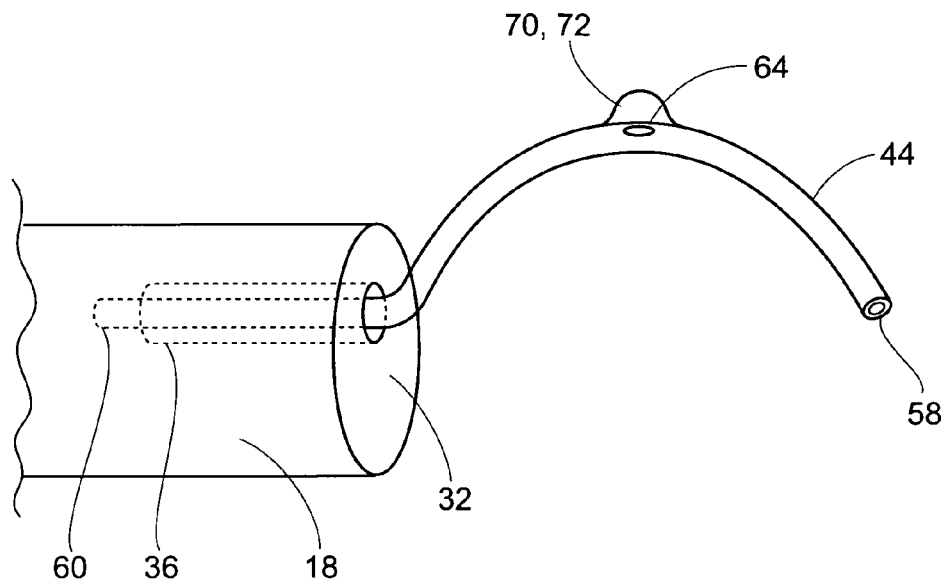
FIG. 6A is a lateral view of the junction between the basket arms and the shaft illustrating the pathway used for advancement of the movable wire or the delivery of fluids.
Figure 6B:
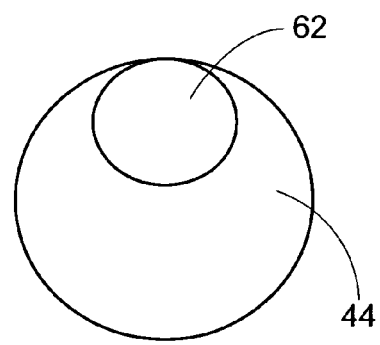
FIG. 6B is a frontal view of a basket arm in an alternative embodiment of the invention illustrating a track in the arm used to advance the movable wire.
Figure 7:
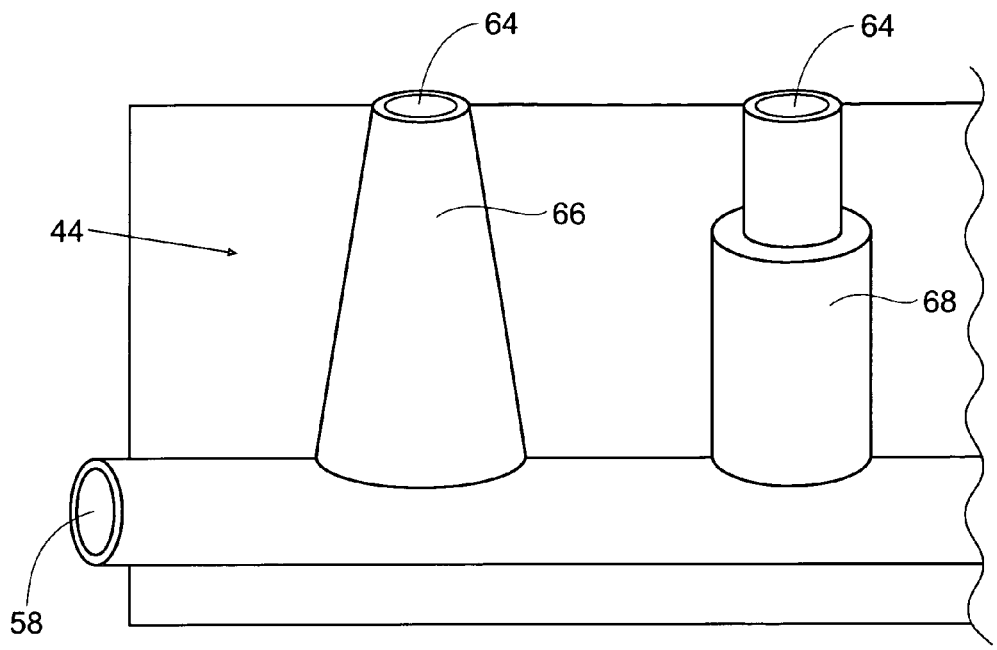
FIG. 7 is a cross-sectional view of a section of the basket arm illustrating stepped and tapered sections in basket arm apertures.

Referring now to FIG. 6A, arms 44 may also be solid or hollow with a continuous lumen 58 that may be coupled with shaft lumens 36. These coupled lumens provide a path for the delivery of a fluid or electrode delivery member 60 from shaft 18 to any point on expandable mapping assembly 20. In various embodiments electrode delivery member 60 can be an insulated wire, an insulated guide wire, a plastic-coated stainless steel hypotube with internal wiring or a plastic catheter with internal wiring, all of which are known to those skilled in the art. As shown in FIG. 6B, arms 44 may also have a partially open channel 62, also called a track 62, that functions as a guide track for electrode delivery member 60. Referring back to FIG. 6A, arms 44 may have one or more apertures 64 at any point along their length that permit the controlled placement of electrodes 88 at or into sphincter wall 26. Referring now to FIG. 7, apertures 64 may have stepped sections 66 or tapered sections 68 in all or part of their length, that are used to control the penetration depth of electrodes 88 into sphincter wall 26. Referring back to FIG. 6A, apertures 64 in combination with arm lumens 58 and shaft lumens 36 may be used for the delivery of cooling solution 70 or electrolytic solution 72 to treatment site 12 as described herein. Additionally, arms 44 can also carry a plurality of longitudinally or radially spaced apart radiopaque and or echogenic markers or traces, not shown in the drawings, formed of suitable materials to permit viewing of basket assembly 50 via fluoroscopy or ultrasonography. Suitable radiopaque materials include platinum or gold, while suitable echogenic materials include gas filled microparticles as described in US Pat. Nos. 5,688,490 and 5,205,287. Arms 44 may also be color-coded to facilitate their identification via visual medical imaging methods and equipment, such as endoscopic methods, which are well known to those skilled in the art.

Figure 8:
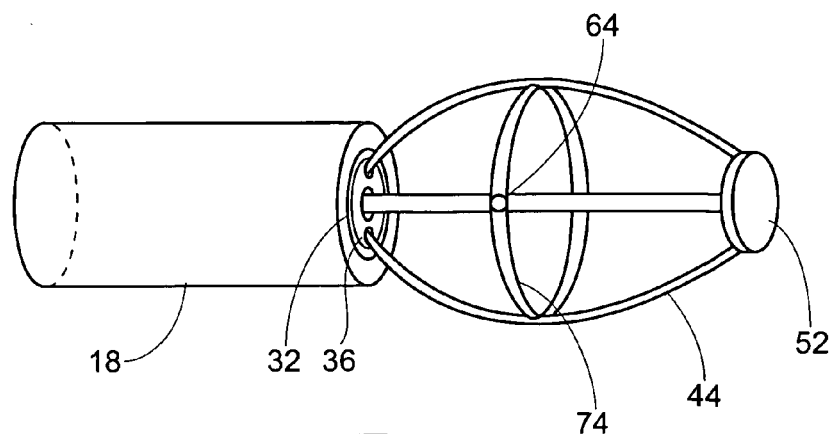
FIG. 8 is a lateral view of the basket assembly illustrating the placement of the radial supporting member.

In another embodiment of the present invention, a radial supporting member 74 is attached to two or more arms 44. Radial supporting member 74, also called a strut, can be attached to arms 44 along a circumference of basket assembly 50 as shown in FIG. 8. Apertures 64 can extend through radial supporting member 74 in one or more places. Radial supporting member 74 serves the following functions: i) facilitates opening and effacement of the folds of sphincter 16, ii) enhances contact of apertures 64 with sphincter wall 26; and, iii) reduces or prevents the tendency of arms 44 to bunch up. The cross sectional geometry of radial supporting member 74 can be rectangular or circular, though it will be appreciated that other geometries are equally suitable.

Figure 9A:
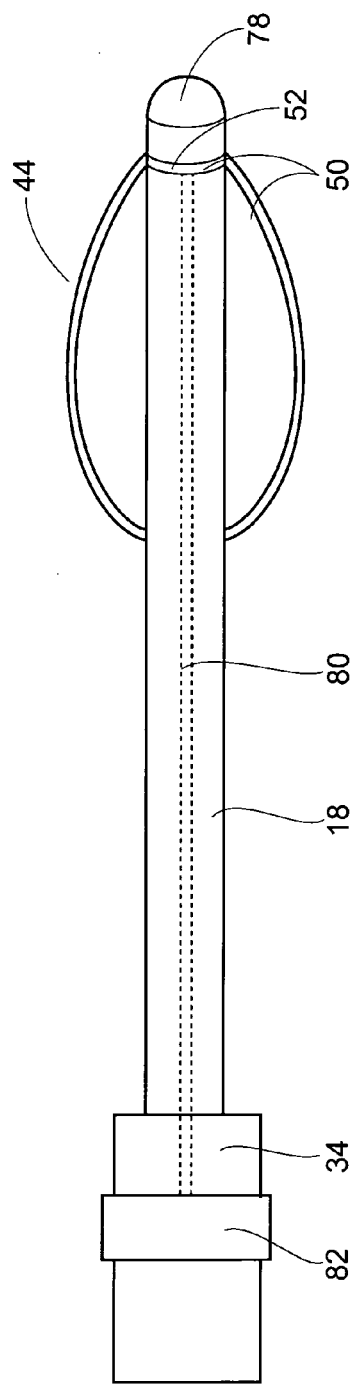
FIG. 9A is a lateral view of the sphincter mapping and treatment apparatus illustrating the mechanism used in one embodiment of the invention to increase the camber of the basket assembly.
Figure 9B:
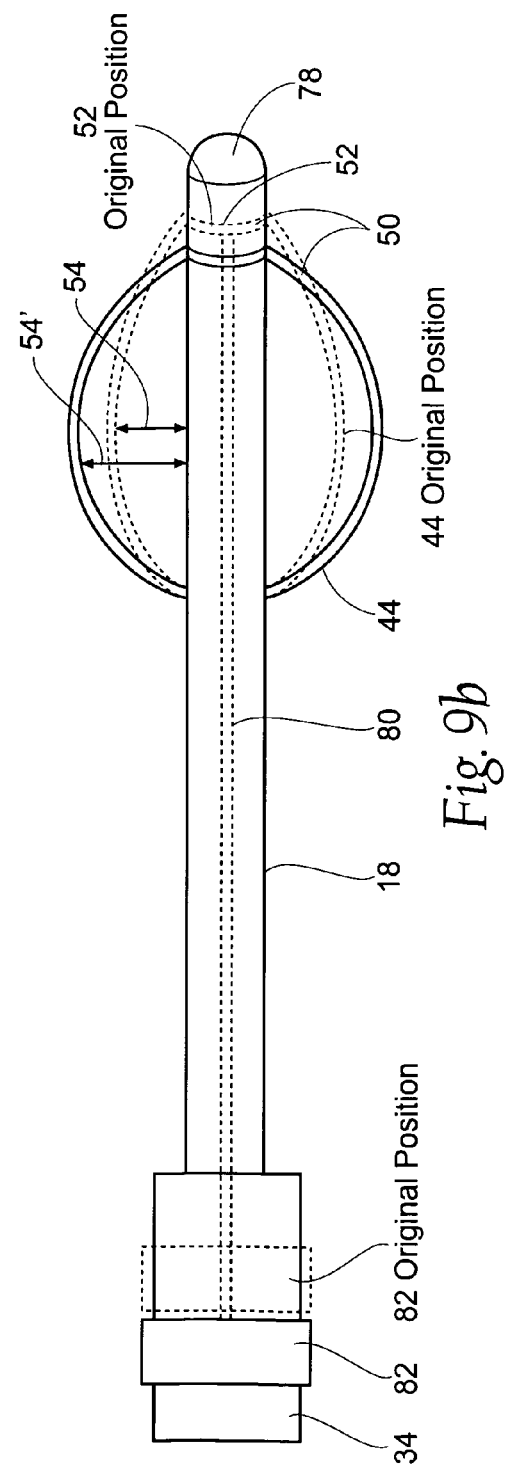
FIG. 9B is a similar view to 9A showing the basket assembly in an increased state of camber.
Figure 10:
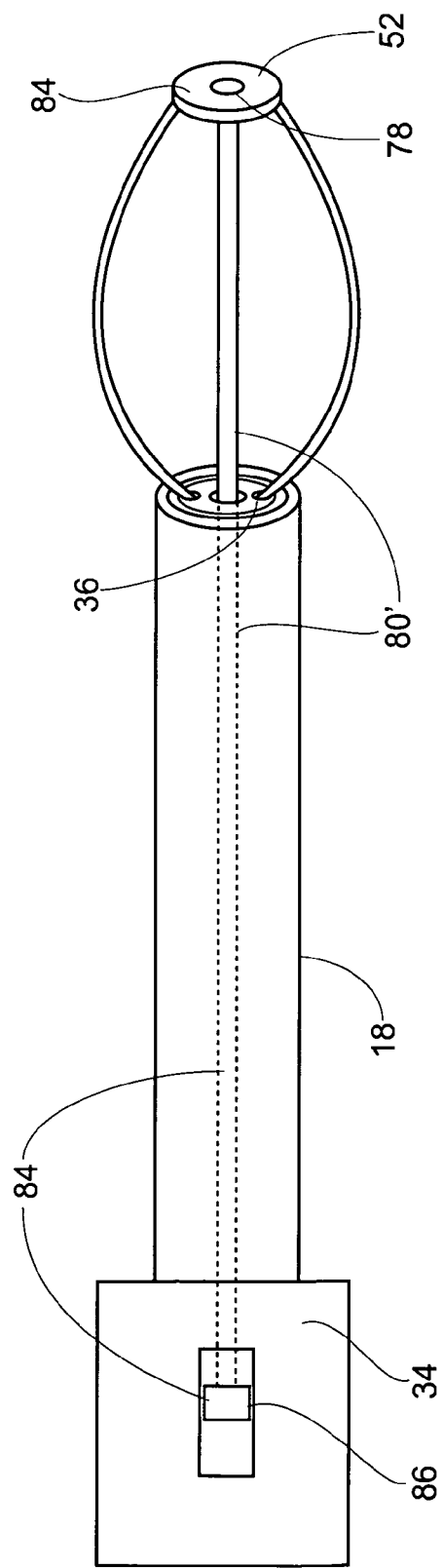
FIG. 10 is a lateral view of the sphincter mapping and treatment apparatus illustrating the deflection mechanism.

In one embodiment shown in FIG. 9, arms 44 are attached to distal basket cap 52 that in turn, moves freely over shaft 18, but is stopped distally by shaft cap 78. One or more pull wires 80 are attached to distal basket cap 52 and also to a movable fitting 82 in proximal fitting 34 of sphincter mapping and treatment apparatus 10. When pull wire 80 is pulled back by movable fitting 82, the camber 54 of basket assembly 50 increases to 54', increasing the force and the amount of contact applied by basket assembly 50 to sphincter wall 26 or an adjoining structure. Basket assembly 50 can also be deflected from side to side using deflection mechanism 84. This allows the physician to remotely point and steer the basket assembly within the body. In one embodiment shown in FIG. 10, deflection mechanism 84 includes a second pull wire 80' attached to shaft cap 78 and also to a movable slide 86 integral to proximal fitting 34.

Turning now to a discussion of energy delivery, suitable power sources 56 and electrodes 88 that can be employed in one or more embodiments of the invention include: (i) a radio-frequency (RF) source coupled to an RF electrode, (ii) a coherent source of light coupled to an optical fiber, (iii) an incoherent light source coupled to an optical fiber, (iv) a heated fluid coupled to a catheter with a closed channel configured to receive the heated fluid, (v) a heated fluid coupled to a catheter with an open channel configured to receive the heated fluid, (vi) a cooled fluid coupled to a catheter with a closed channel configured to receive the cooled fluid, (vii) a cooled fluid coupled to a catheter with an open channel configured to receive the cooled fluid, (viii) a cryogenic fluid, (ix) a resistive heating source, (x) a microwave source providing energy from 915 MHz to 2.45 GHz and coupled to a microwave antenna, (xi) an ultrasound power source coupled to an ultrasound emitter, wherein the ultrasound power source produces energy in the range of 300 KHZ to 3 GHz, or (xii) a microwave source. For ease of discussion for the remainder of this application, the power source utilized is an RF source and electrode 88 is one or more RF electrodes 88. However, all of the other herein mentioned power sources and mapping electrodes are equally applicable to sphincter mapping and treatment apparatus 10.

For the case of RF energy, RF electrode 88 may operated in either bipolar or monopolar mode with a ground pad electrode. In a monopolar mode of delivering RF energy, a single electrode 88 is used in combination with an indifferent electrode patch that is applied to the body to form the other electrical contact and complete an electrical circuit. Bipolar operation is possible when two or more RF electrodes 88 are used. Multiple RF electrodes 88 may be used. These electrodes may be cooled as described herein. RF electrodes 88 can be attached to electrode delivery member 60 by the use of soldering methods which are well known to those skilled in the art. Suitable solders include Megabond Solder supplied by the Megatrode Corporation (Milwaukee, Wis.).

Figure 11:
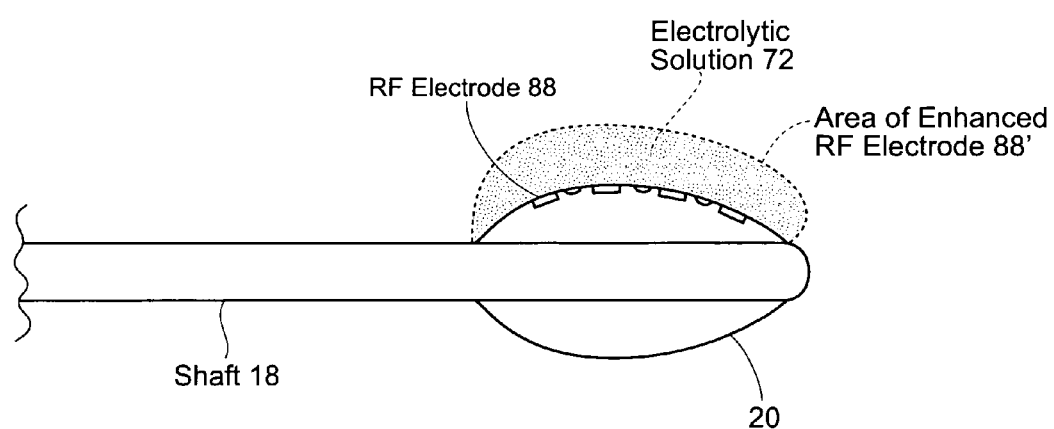
FIG. 11 is a lateral view illustrating the use of electrolytic solution to create an enhanced RF electrode.

Suitable electrolytic solutions 72 include saline, solutions of calcium salts, potassium salts, and the like. Electrolytic solutions 72 enhance the electrical conductivity of the targeted tissue at the treatment site 12. When a highly conductive fluid such as electrolytic solution 72 is infused into tissue the electrical resistance of the infused tissue is reduced, in turn, increasing the electrical conductivity of the infused tissue. As a result, there will be little tendency for tissue surrounding electrode 88 to desiccate (a condition described herein that increases the electrical resistance of tissue) resulting in a large increase in the capacity of the tissue to carry RF energy. Referring to FIG. 11, a zone of tissue which has been heavily infused with a concentrated electrolytic solution 72 can become so conductive as to actually act as an enhanced electrode 88'. The effect of enhanced electrode 88' is to increase the amount of current that can be conducted to the treatment site 12, making it possible to heat a much greater volume of tissue in a given time period.

Also when the power source is RF, power source 56, which will now be referred to as RF power source 56, may have multiple channels, delivering separately modulated power to each electrode 88. This reduces preferential heating that occurs when more energy is delivered to a zone of greater conductivity and less heating occurs around RF electrodes 88 which are placed into less conductive tissue. If the level of tissue hydration or the blood infusion rate in the tissue is uniform a single channel RF power source 56 may be used to provide power for generation of lesions 14 relatively uniform in size.

RF electrodes 88 can have a variety of shapes and sizes. Possible shapes include, but are not limited to, circular, rectangular, conical and pyramidal. Electrode surfaces can be smooth or textured and concave or convex. The conductive surface area of electrode 88 can range from 0.1 mm$^2$ to 100 cm$^2$. It will be appreciated that other geometries and surface areas may be equally suitable.

In one embodiment, RF electrodes 88 can be in the shape of needles and of sufficient sharpness and length to penetrate into the smooth muscle of the esophageal wall, sphincter 16 or other anatomical structure. In this embodiment shown in FIGS. 12 and 13, needle electrodes 90 are attached to arms 44 and have an insulating layer 92, covering an insulated segment 94 except for an exposed segment 95. For purposes of this disclosure, an insulator or insulation layer is a barrier to either thermal, RF or electrical energy flow. Insulated segment 94 is of sufficient length to extend into sphincter wall 26 and minimize the transmission of RF energy to a protected site 97 near or adjacent to insulated segment 94 (see FIG. 13). Typical lengths for insulated segment 94 include, but are not limited to, 1–4 mm. Suitable materials for needle electrodes 90 include, but are not limited to, 304 stainless steel and other stainless steels known to those skilled in the art. Suitable materials for insulating layer 92 include, but are not limited to, polyimides and polyamides.

Figure 14A:
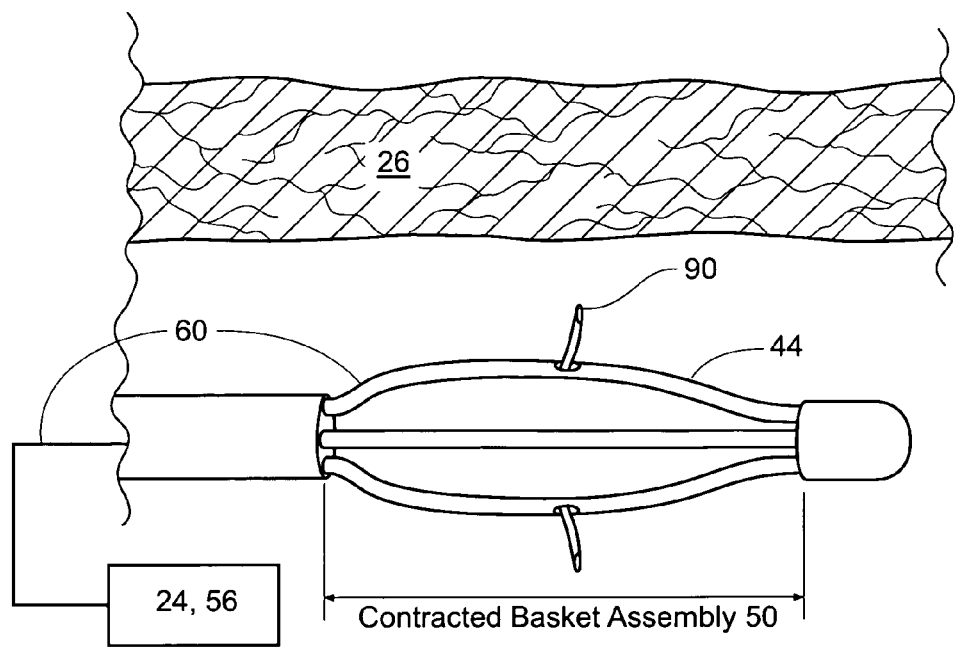
FIG. 14 is a lateral view illustrating the placement of needle electrodes into the sphincter wall by expansion of the basket assembly.
Figure 14B:
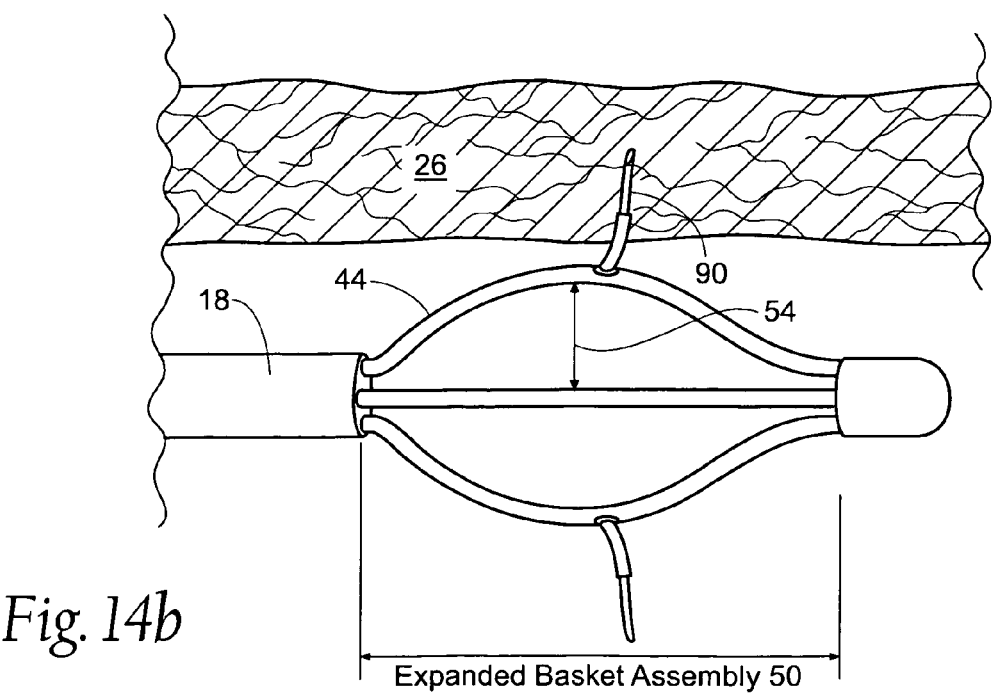

During introduction of sphincter mapping and treatment apparatus 10, basket assembly 50 is in a contracted state. Once sphincter mapping and treatment apparatus 10 is properly positioned at the treatment site 12, needle electrodes 90 are deployed by expansion of basket assembly 50, resulting in the protrusion of needle electrodes 90 into the smooth muscle tissue of sphincter wall 26 (refer to FIG. 14). The depth of needle penetration is selectable from a range of 0.5 to 5 mm and is accomplished by indexing movable fitting 82 so as to change the camber 54 of arm 44 in fixed increments that can be selectable in a range from 0.1 to 4 mms. Needle electrodes 90 are coupled to power source 56 via insulated wire 60.

Figure 15:
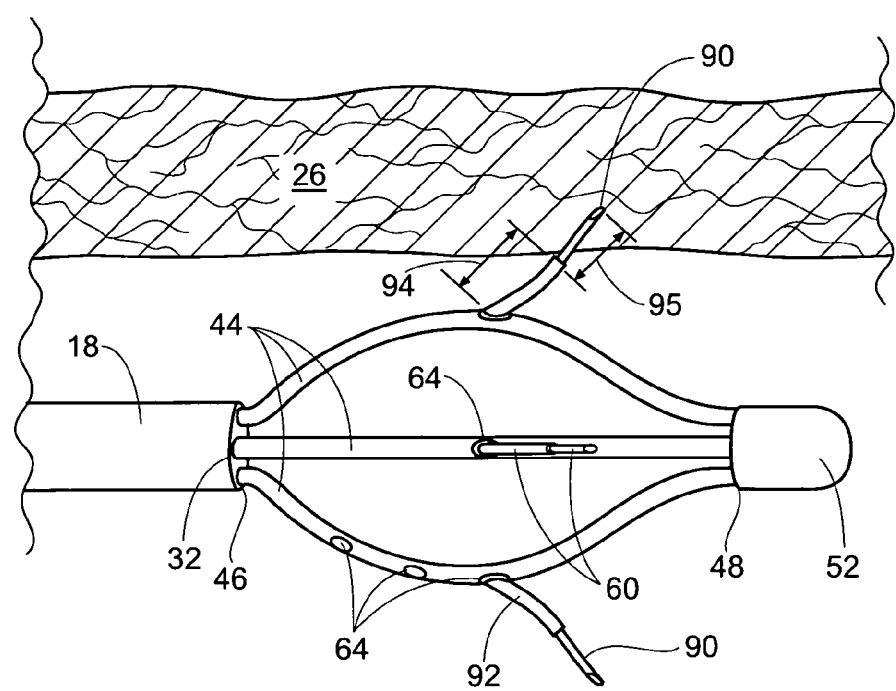
FIG. 15 is a lateral view illustrating placement of needle electrodes into the sphincter wall by advancement of an electrode delivery member out of apertures in the basket arms.
Figure 16:
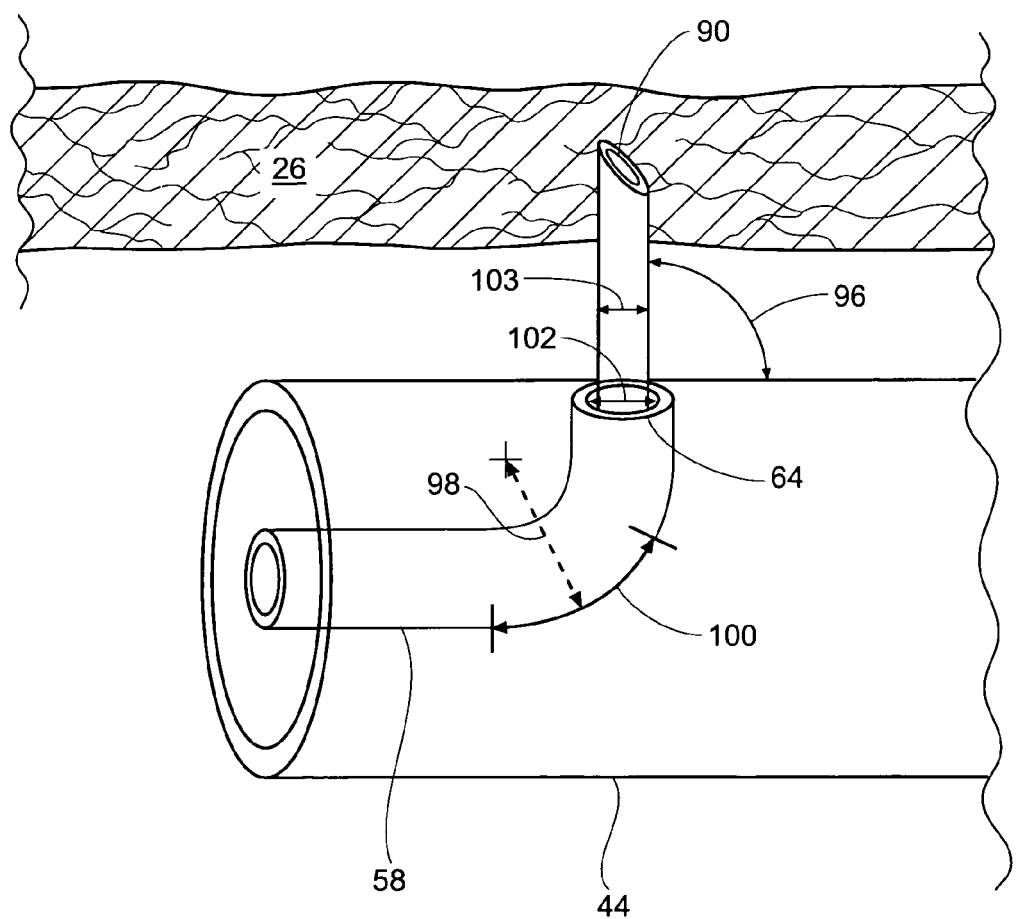
FIG. 16 is a cross sectional view illustrating the configuration of a basket arm aperture used to select and maintain a penetration angle of the needle electrode into the sphincter wall.

In another embodiment of sphincter mapping and treatment apparatus 10 shown in FIG. 15, needle electrodes 90 are advanced out of apertures 64 in basket arms 44 into the smooth muscle of the esophageal wall or other sphincter 16. In this case, needle electrodes 90 are electrically coupled to RF power source 56 by electrode delivery member 60. In this embodiment, the depth of needle penetration is selectable via means of stepped sections 66 or tapered sections 68 located in apertures 64. Referring to FIG. 16, apertures 64 and needle electrodes 90 are configured such that the penetration angle 96 (also called an emergence angle 96) of needle electrode 90 into sphincter wall 26 remains sufficiently constant during the time needle electrode 90 is being inserted into sphincter wall 26, such that there is no tearing or unnecessary trauma to sphincter wall tissue. This is facilitated by the selection of the following parameters and criteria: i) the emergence angle 96 of apertures 64 which can vary from 1 to 90°, ii) the arc radius 98 of the curved section 100 of aperture 64 which can vary from 0.001 to 2 inch, iii) the amount of clearance between the aperture inner diameter 102 and the needle electrode outside diameter 103 which can very between 0.001" and 0.1"; and, iv) use of a lubricous coating on electrode delivery member 60 such as a Teflon® or other coatings well known to those skilled in the art. Also in this embodiment, insulated segment 94 can be in the form of an sleeve that may be adjustably positioned at the exterior of needle electrode 90.

Figure 17:
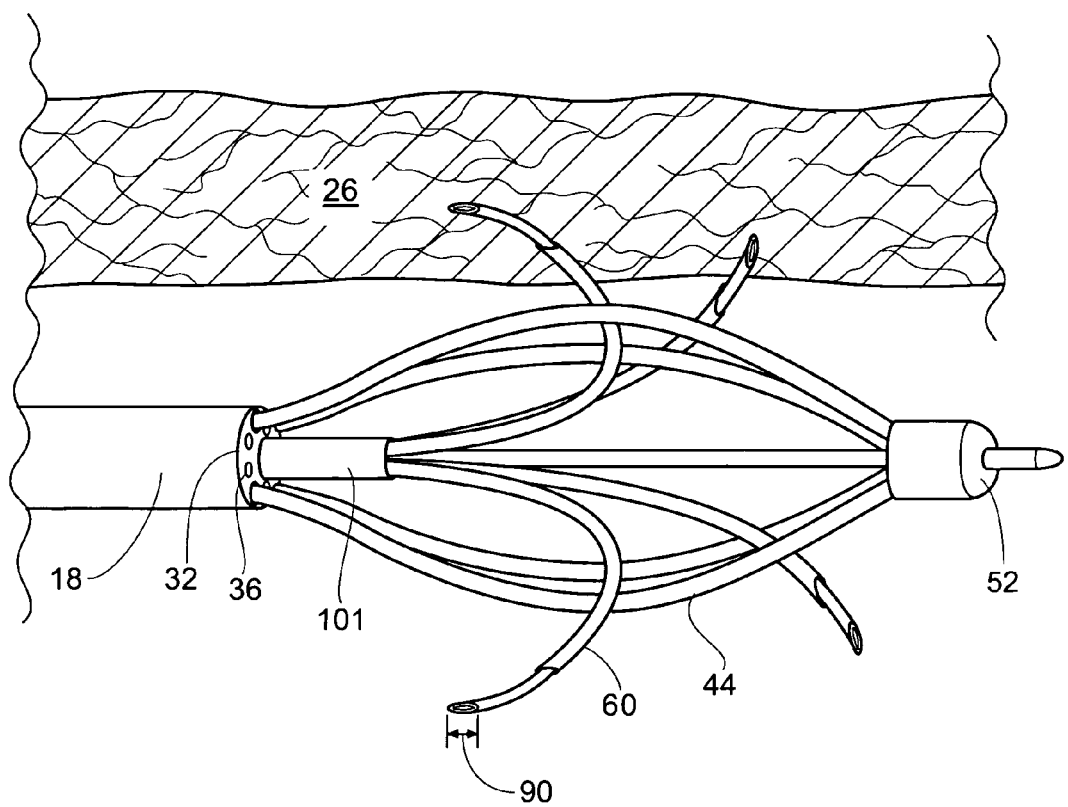
FIG. 17 is a lateral view illustrating placement of needle electrodes into the sphincter wall by advancement of an electrode delivery member directly out of the distal end of the shaft.
Figure 18A:
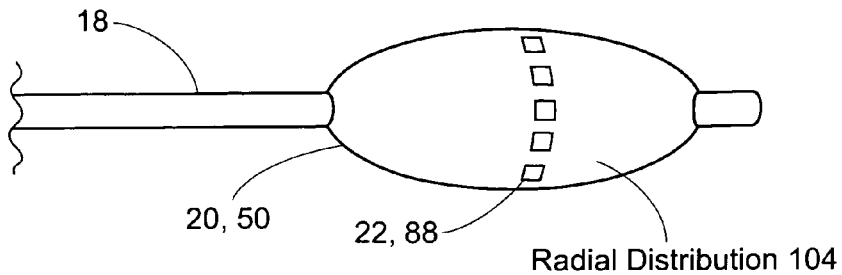
FIG. 18A is a lateral view illustrating a radial distribution of electrodes on the expandable mapping assembly of the invention.
Figure 18B:
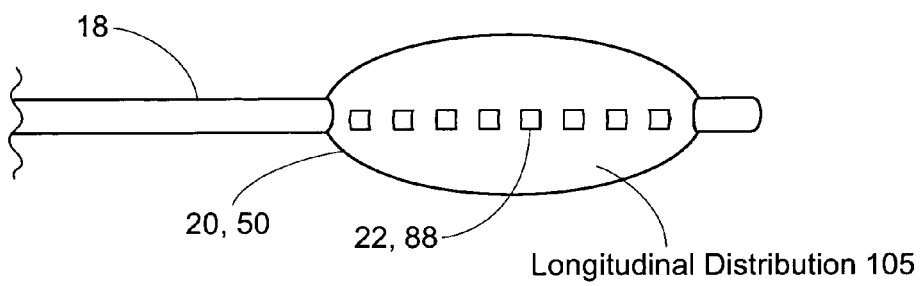
FIG. 18B is a lateral view illustrating a longitudinal distribution of electrodes on the expandable mapping assembly of the invention.
Figure 18C:
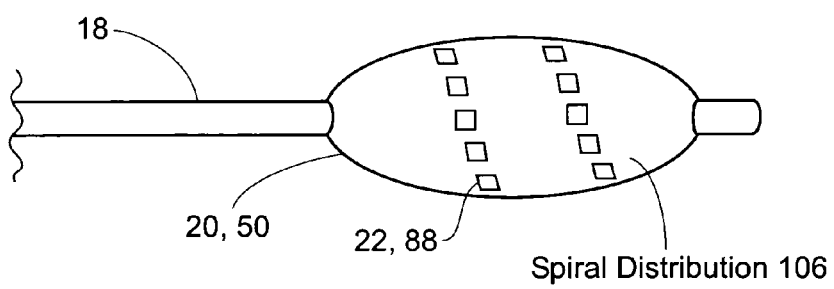
FIG. 18C is a lateral view illustrating a spiral distribution of electrodes on the expandable mapping assembly of the invention.
Figure 18D:
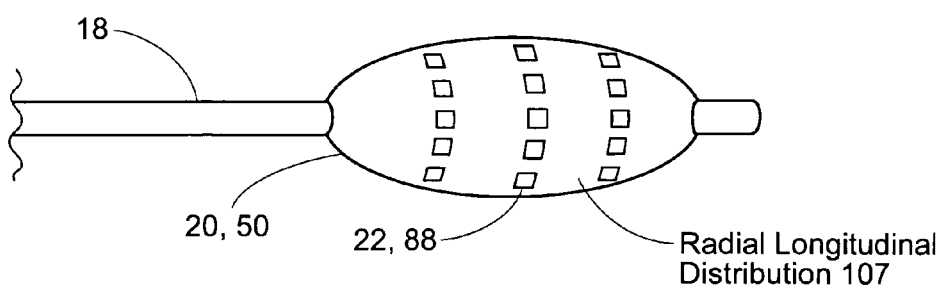
FIG. 18D is a lateral view illustrating a radial-longitudinal distribution of electrodes on the expandable mapping assembly of the invention.

In another alternative embodiment shown in FIG. 17, electrode delivery member 60 with attached needle electrodes 90, can exit from shaft lumen 36 at distal shaft end 32 and be positioned into contact with sphincter wall 26. This process may be facilitated by use of a hollow guiding member 101, known to those skilled in the art as a guiding catheter, through which electrode delivery member 60 is advanced. Guiding catheter 101 may also include stepped sections 66 or tapered sections 68 at it distal end to control the depth of penetration of needle electrode 90 into sphincter wall 26.

RF energy flowing through tissue causes heating of the tissue due to absorption of the RF energy by the tissue and ohmic heating due to electrical resistance of the tissue. This heating can cause injury to the affected cells and can be substantial enough to cause cell death, a phenomenon also known as cell necrosis. For ease of discussion for the remainder of this application, cell injury will include all cellular effects resulting from the delivery of energy from electrode 88 up to, and including, cell necrosis. Cell injury can be accomplished as a relatively simple medical procedure with local anesthesia. In one embodiment, cell injury proceeds to a depth of approximately 1–4 mm from the surface of the mucosal layer of sphincter 16 or that of an adjoining anatomical structure.

Referring now to FIGS. 18A, 18B, 18C and 18D, mapping electrodes 22, RF electrodes 88 and/or apertures 64 may be distributed in a variety of patterns along expandable mapping assembly 20 or basket assembly 50 to facilitate mapping and in order to produce a desired placement and pattern of lesions 14. Typical electrode (both mapping and RF varieties) and aperture distribution patterns include, but are not limited to, a radial distribution 104 (refer to FIG. 18A), a longitudinal distribution 105 (refer to FIG. 18B), a spiral distribution 106 (refer to FIG. 18C) and a combination of longitudinal and radial distributions 107 (refer to FIG. 18D). It will be appreciated that other combinations, patterns and geometries for electrode and aperture placement, may also be suitable. These electrodes may be cooled as described hereafter.

Figure 19:
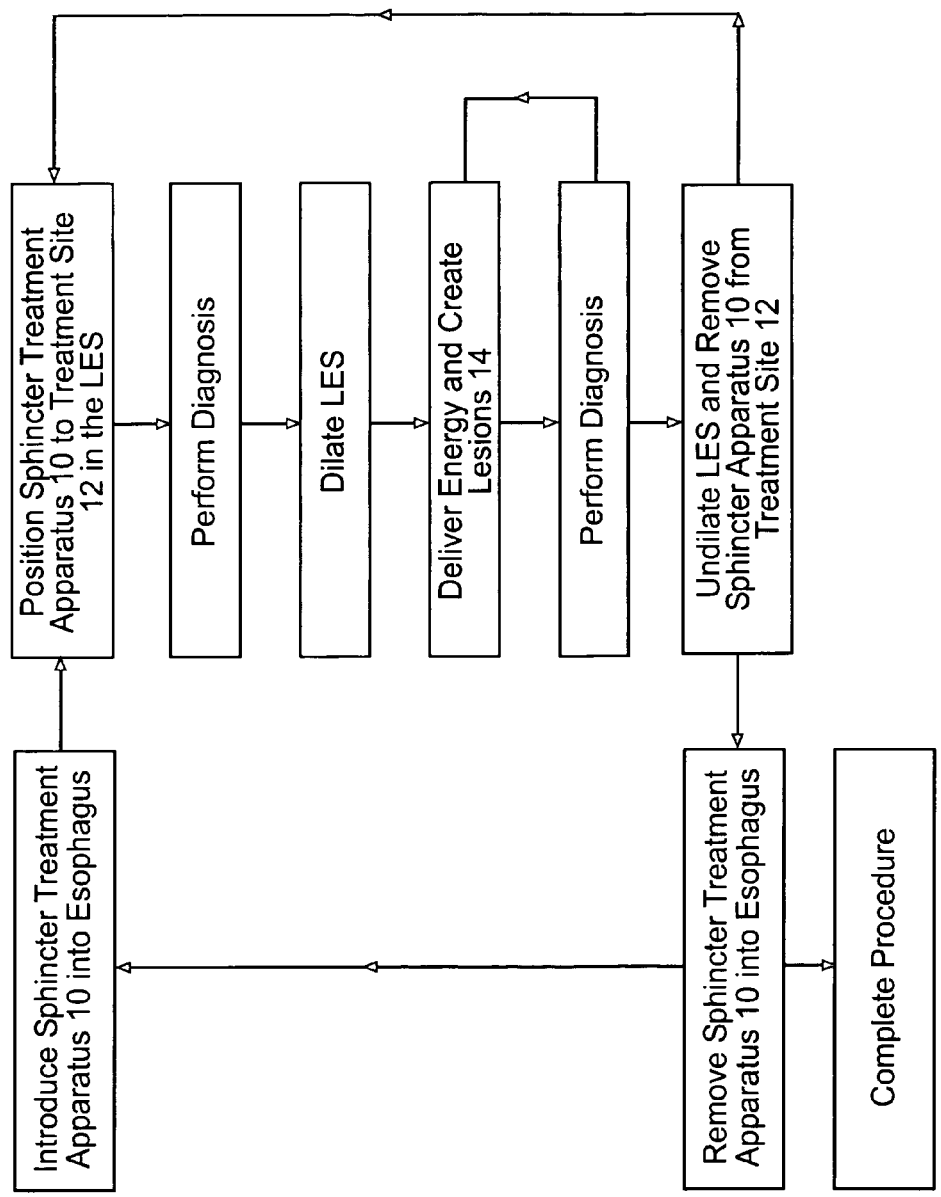
FIG. 19 is a flow chart illustrating a sphincter treatment method.

FIG. 19 is a flow chart illustrating one embodiment of the procedure for using sphincter mapping and treatment apparatus 10. In this embodiment, sphincter mapping and treatment apparatus 10 is first introduced into the esophagus under local anesthesia. Sphincter mapping and treatment apparatus 10 can be introduced into the esophagus by itself or through a lumen in an endoscope (not shown), such as disclosed in U.S. Pat. Nos. 5,448,990 and 5,275,608, incorporated herein by reference, or similar esophageal access device known to those skilled in the art. Basket assembly 50 is expanded as described herein. This serves to temporarily dilate the LES or sufficiently to efface a portion of or all of the folds of the LES. In an alternative embodiment, esophageal dilation and subsequent LES fold effacement can be accomplished by insufflation of the esophagus (a known technique) using gas introduced into the esophagus through shaft lumen 36, or an endoscope or similar esophageal access device as described above. Once treatment is completed, basket assembly 50 is returned to its predeployed or contracted state and sphincter mapping and treatment apparatus 10 is withdrawn from the esophagus. This results in the LES returning to approximately its pretreatment state and diameter. It will be appreciated that the above procedure is applicable in whole or part to the treatment of other sphincters in the body.

Figure 20:
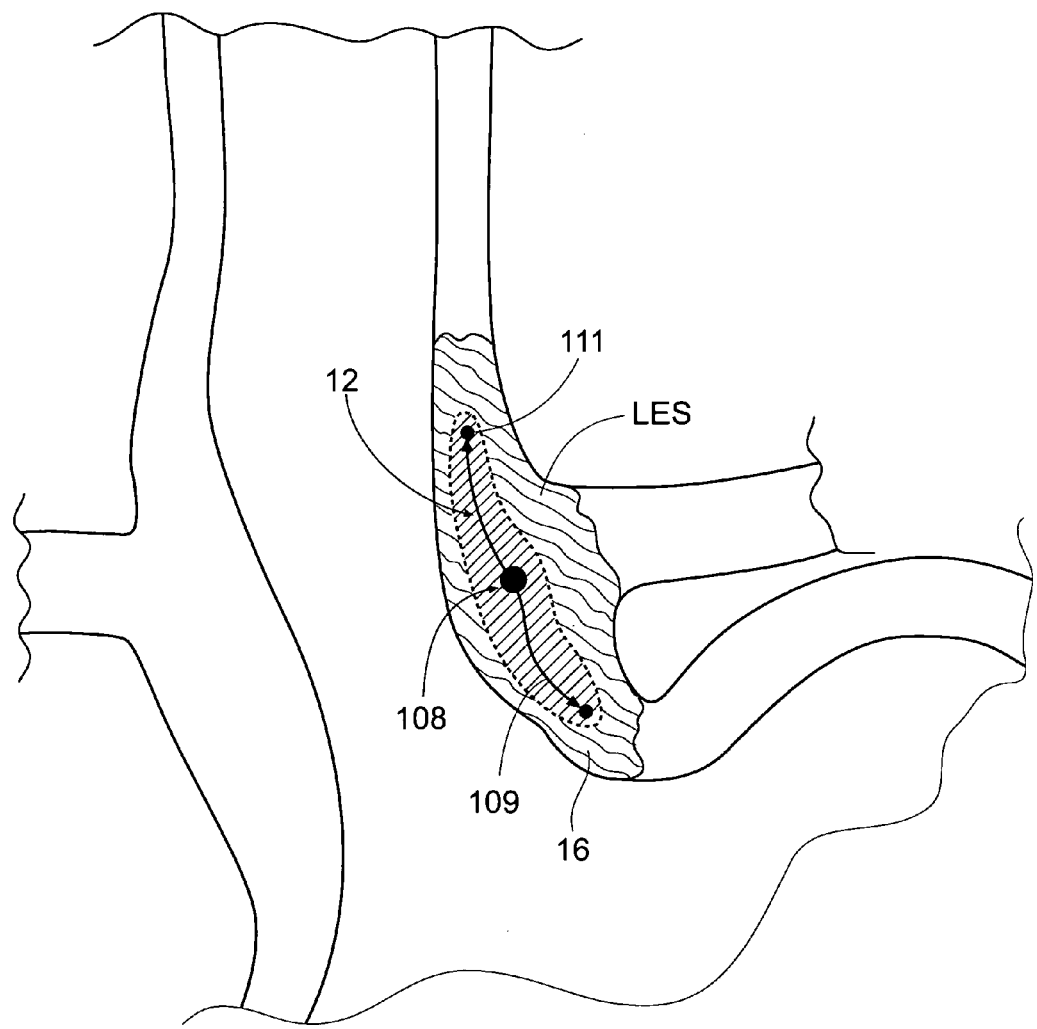
FIG. 20 is a lateral view of sphincter smooth muscle tissue illustrating electromagnetic foci and pathways for the origination and conduction of aberrant electrical signals in the smooth muscle of the lower esophageal sphincter or other tissue.

As discussed previously, controller 24 and electropotential map 27 are used to by the physician to diagnose abnormalities and pathologies within sphincter 16 and adjoining structures. More specifically, they are used to identify electrical events that include depolarization, contraction and repolarization. This information is used by the physician to determine target treatment sites 12 in the LES or adjoining anatomical structures that are acting as foci 108 or pathways 109 for aberrant electrical signals 111 causing abnormal or otherwise inappropriate relaxation of the smooth muscle of the LES or other sphincter 16 (Refer to FIG. 20). These targeted treatment sites 12 are then treated as described herein so as to create lesions 14 which disrupt, block or otherwise prevent the generation and transmission of sufficient aberrant electrical signals 111 to cause relaxation of the LES or other sphincter wall 26.

A variety of other diagnostic methods can be employed as an adjunct to surface mapping of sphincter wall 26. These method include, but are not limited to, the following: (i) visualization of the interior surface of the esophagus via an endoscope or other viewing apparatus inserted into the esophagus, (ii) visualization of the interior morphology of the esophageal wall using ultrasonography to establish a baseline for the tissue to be treated; and, (iii) impedance measurement to determine the electrical conductivity between the esophageal mucosal layers and sphincter mapping and treatment apparatus 10.

In the treatment phase of the procedure, the delivery of energy to treatment site 12 can be conducted under feedback control, manually or by a combination of both. Feedback control (described herein) enables sphincter mapping and treatment apparatus 10 to be positioned and retained in the esophagus during treatment with minimal attention by the physician. RF electrodes 88 can be multiplexed in order to treat the entire targeted treatment site 12 or only a portion thereof Feedback can be included and is achieved by the use of one or more of the following methods: (i) visualization, (ii) impedance measurement, (iii) ultrasonography, (iv) temperature measurement; and, (v) sphincter contractile force measurement via manometry. The feedback mechanism permits the selected on-off switching of different RF electrodes 88 in a desired pattern, which can be sequential from one electrode 88 to an adjacent electrode 88, or can jump around between non-adjacent RF electrodes 88. Individual RF electrodes 88 are multiplexed and volumetrically controlled by controller 23'.

Figure 21:
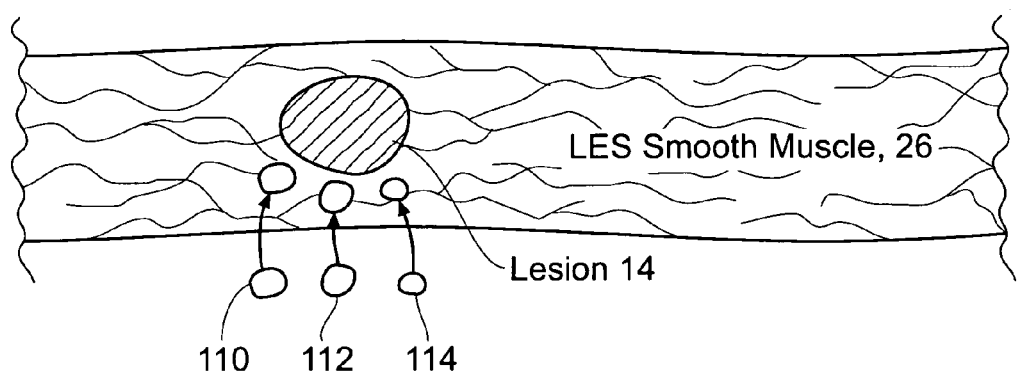
FIG. 21 is a lateral view of a sphincter wall illustrating the infiltration of tissue healing cells into a lesion in the smooth tissue of a sphincter following treatment with the sphincter treatment apparatus of the present invention.
Figure 22:
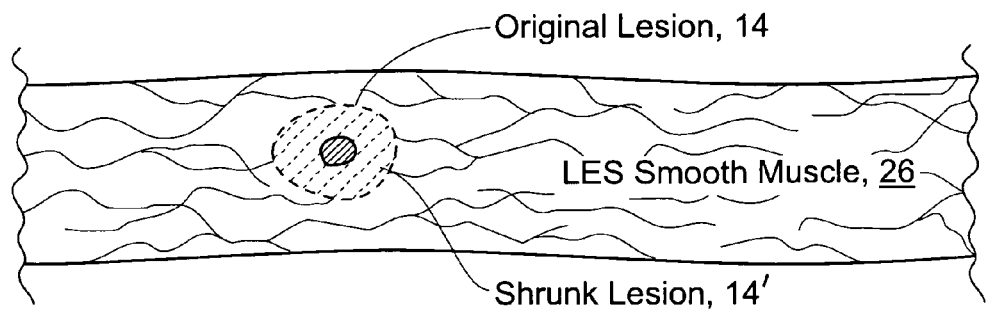
FIG. 22 is a view similar to that of FIG. 21 illustrating shrinkage of the lesion site caused by cell infiltration.

The area and magnitude of cell injury in the LES or sphincter 16 can vary. However, it is desirable to deliver sufficient energy to the targeted treatment site 12 to be able to achieve tissue temperatures in the range of 55–95° C. and produce lesions 14 at depths ranging from 1–4 mm from the interior surface of the LES or sphincter wall 26. Typical energies delivered to the esophageal wall include, but are not limited to, a range between 100 and 50,000 joules per electrode 88. It is also desirable to deliver sufficient energy such that the resulting lesions 14 have a sufficient magnitude and area of cell injury to cause an infiltration of lesion 14 by fibroblasts 110, myofibroblasts 112, macrophages 114 and other cells involved in the tissue healing process (refer to FIG. 21). As shown in FIG. 22, these cells cause a contraction of tissue around lesion 14, decreasing its volume and, or altering the biomechanical properties at lesion 14 so as to result in a tightening of LES or sphincter 16. These changes are reflected in transformed lesion 14' shown in FIG. 19B.

Figure 23:
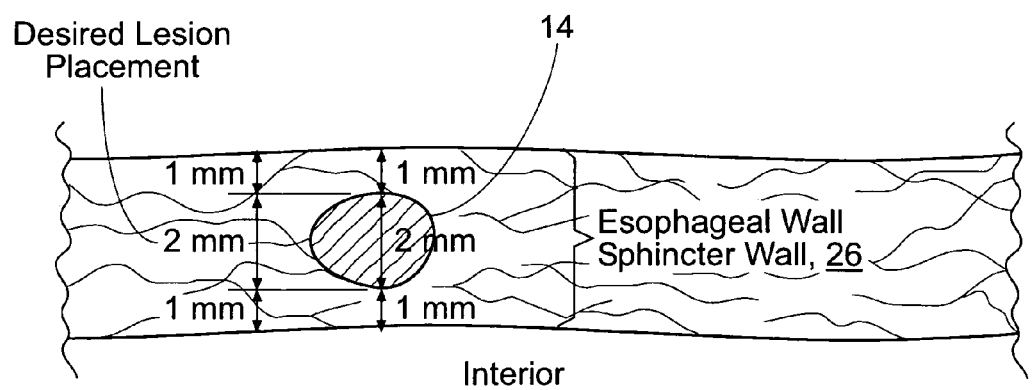
FIG. 23 is a lateral view of the esophageal wall illustrating the preferred placement of lesions in the smooth muscle layer of a esophageal sphincter.

The diameter of lesions 14 can vary between 0.1 to 4 mm It is preferable that lesions 14 are less than 4 mm in diameter in order to reduce the risk of thermal damage to the mucosal layer. In one embodiment, a 2 mm diameter lesion 14 centered in the wall of the smooth muscle provides a 1 mm buffer zone to prevent damage to the mucosa, submucosa and adventitia, while still allowing for cell infiltration and subsequent sphincter tightening on approximately 50% of the thickness of the wall of the smooth muscle (refer to FIG. 23).

Figure 24:
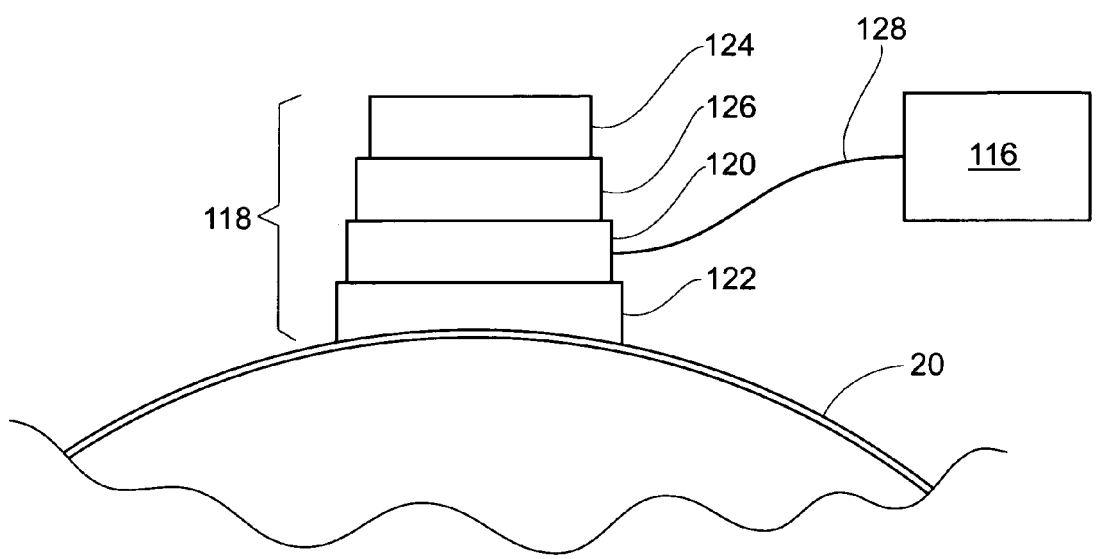
FIG. 24 is a lateral view illustrating the ultrasound transducer, ultrasound lens and power source of an embodiment of the present invention.
Figure 25B:
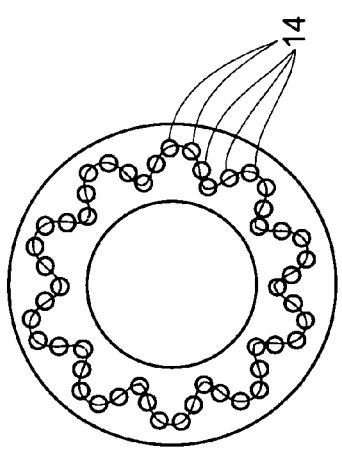
FIGS. 25A–D are lateral views of the sphincter wall illustrating various patterns of lesions created by the apparatus of the present invention.
Figure 25D:
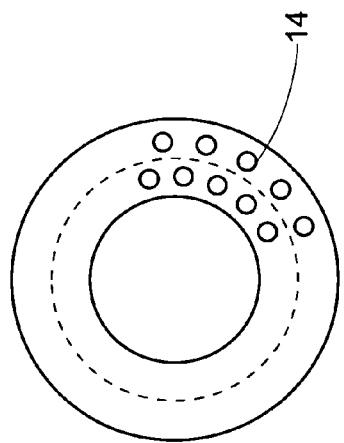
Figure 25A:
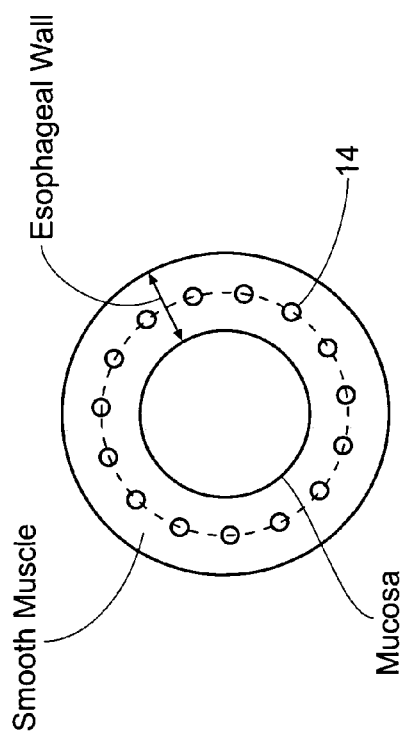
Figure 25C:
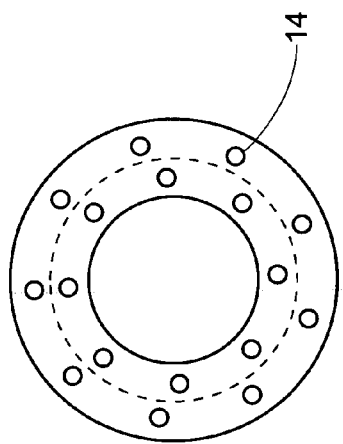

From a diagnostic standpoint, it is desirable to image the interior surface and wall of the LES or other sphincter 16, including the size and position of created lesions 14. It is desirable to create a map of these structures which can be inputed to controller 23' and used to direct the delivery of energy to treatment site 12. Referring to FIG. 24, this can be accomplished through the use of ultrasonography (a known procedure) which involves the use of an ultrasound power source 116 coupled to one or more ultrasound transducers 118 that are positioned on expandable mapping assembly 20 or basket assembly 50. An output is associated with ultrasound power source 116.

Each ultrasound transducer 118 can include a piezoelectric crystal 120 mounted on a backing material 122 that is in turn, attached to expandable mapping assembly 20 or basket assembly 50. An ultrasound lens 124, fabricated on an electrically insulating material 126, is mounted over piezoelectric crystal 120. Piezoelectric crystal 120 is connected by electrical leads 128 to ultrasound power source 116. Each ultrasound transducer 118 transmits ultrasound energy into adjacent tissue. Ultrasound transducers 118 can be in the form of an imaging probe such as Model 21362, manufactured and sold by Hewlett Packard Company, Palo Alto, Calif. In one embodiment, two ultrasound transducers 118 are positioned on opposite sides of expandable mapping assembly 20 or basket assembly 50 to create an image depicting the size and position of lesion 14 in selected sphincter 16.

It is desirable that lesions 14 are predominantly located in the smooth muscle layer of selected sphincter 16 at the depths ranging from 1 to 4 mm from the interior surface of sphincter wall 26. However, lesions 14 can vary both in number and position within sphincter wall 26. It may be desirable to produce a pattern of multiple lesions 14 within the sphincter smooth muscle tissue in order to obtain a selected degree of tightening of the LES or other sphincter 16. Typical lesion patterns shown in FIGS. 25A–D include, but are not limited to, (i) a concentric circle of lesions 14 all at fixed depth in the smooth muscle layer evenly spaced along the radial axis of sphincter 16, (ii) a wavy or folded circle of lesions 14 at varying depths in the smooth muscle layer evenly spaced along the radial axis of sphincter 16, (iii) lesions 14 randomly distributed at varying depths in the smooth muscle, but evenly spaced in a radial direction; and, (iv) an eccentric pattern of lesions 14 in one or more radial locations in the smooth muscle wall. Accordingly, the depth of RF and thermal energy penetration sphincter 16 is controlled and selectable. The selective application of energy to sphincter 16 may be the even penetration of RF energy to the entire targeted treatment site 12, a portion of it, or applying different amounts of RF energy to different sites depending on the condition of sphincter 16. If desired, the area of cell injury can be substantially the same for every treatment event.

Figure 26:
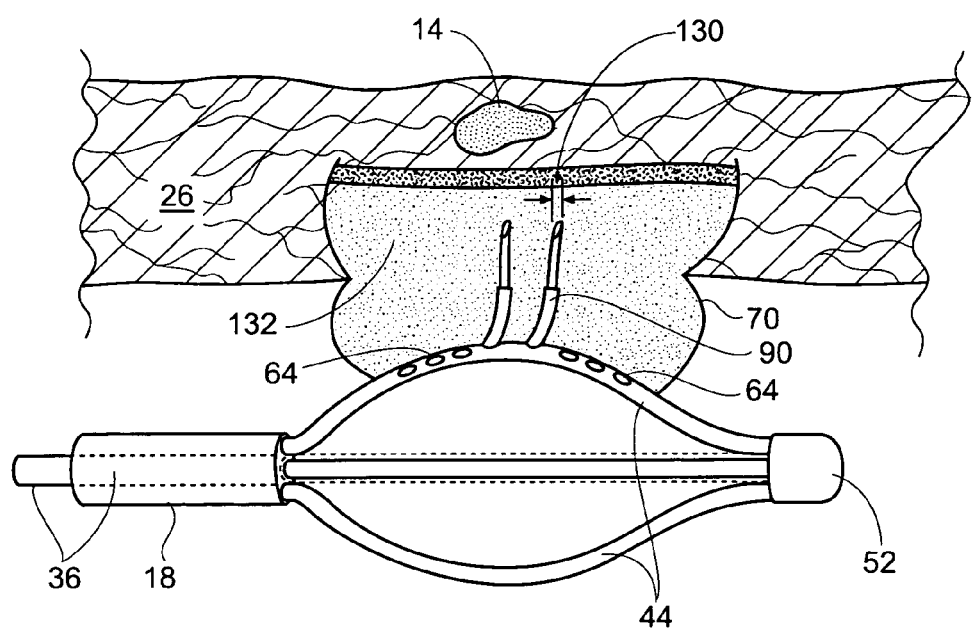
FIG. 26 is a lateral view of the sphincter wall illustrating the delivery of cooling fluid to the electrode-tissue interface and the creation of cooling zones.
Figure 27:
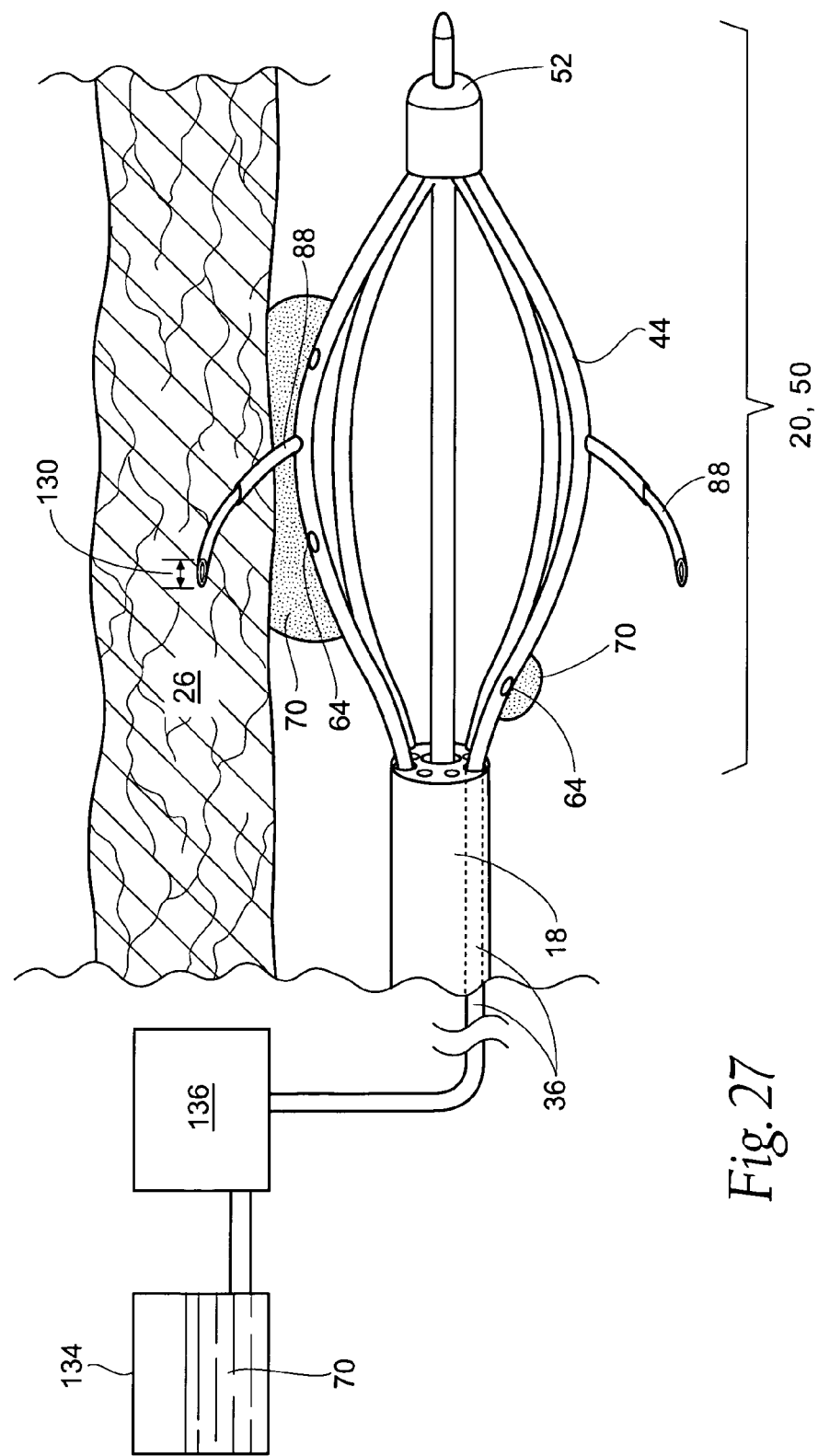
FIG. 27 depicts the flow path, fluid connections and control unit employed to deliver fluid to the electrode-tissue interface.

Referring to FIG. 26, it may be desirable to cool all or a portion of the area near the electrode-tissue interface 130 before, during or after the delivery of energy in order to reduce the degree and area of cell injury. Specifically, the use of cooling preserves the mucosal layers of sphincter wall 26 and protects, or otherwise reduces the degree of cell damage to cooled zone 132 in the vicinity of lesion 14. Referring now to FIG. 27, this can be accomplished through the use of cooling solution 70 that is delivered by apertures 64 which is in fluid communication with shaft lumen 36 that is, in turn, in fluid communication with fluid reservoir 134 and a control unit 136, whose operation is described herein, that controls the delivery of the fluid.

Figure 28:
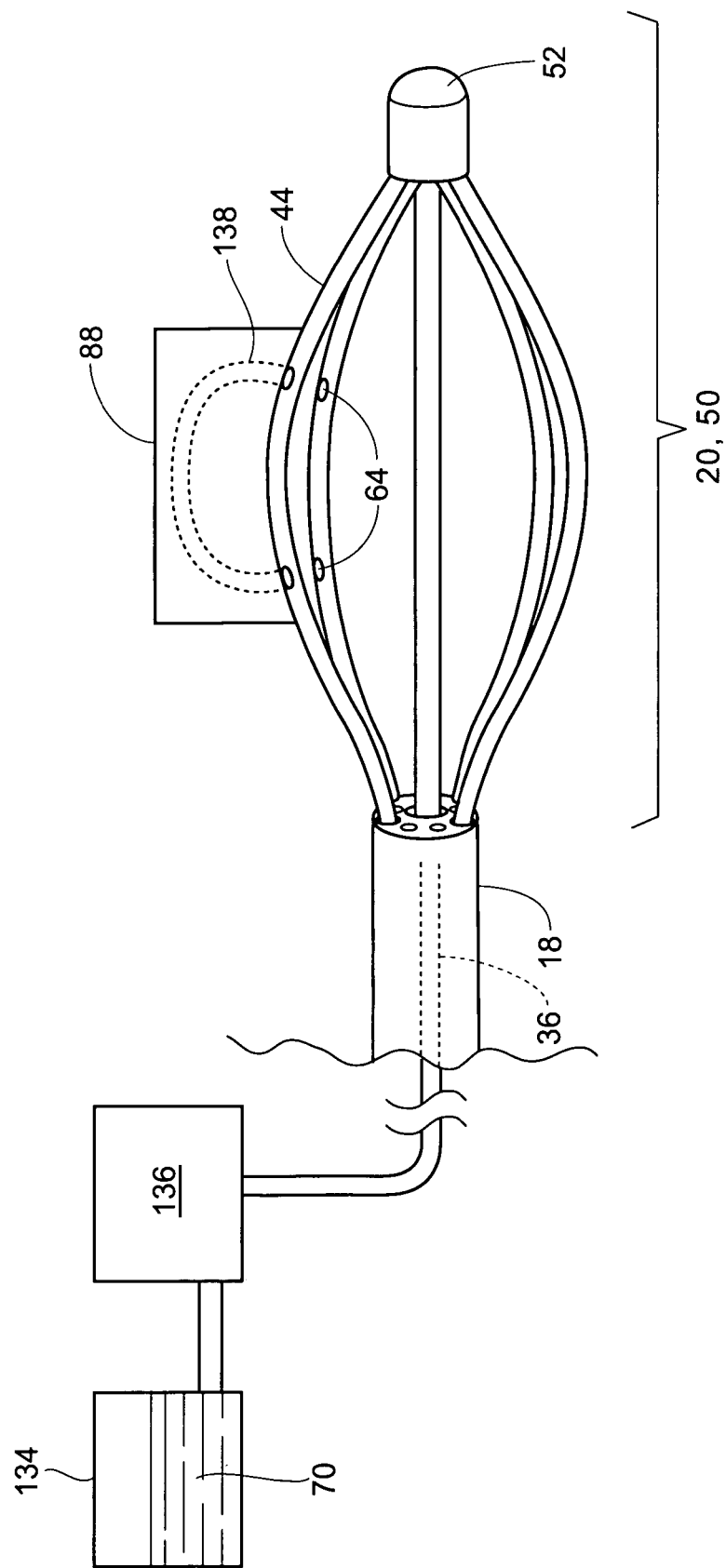
FIG. 28 depicts the flow path, fluid connections and control unit employed to deliver fluid to the RF electrodes.

Similarly, it may also be desirable to cool all or a portion of the electrode 88. The rapid delivery of heat through electrode 88, may result in the build up of charred biological matter on electrode 88 (from contact with tissue and fluids e.g., blood) that impedes the flow of both thermal and electrical energy from electrode 88 to adjacent tissue and causes an electrical impedance rise beyond a cutoff value set on RF power source 56. A similar situation may result from the desiccation of tissue adjacent to electrode 88. Cooling of the electrode 88 can be accomplished by cooling solution 70 that is delivered by apertures 64 as described previously. Referring now to FIG. 28, electrode 88 may also be cooled via a fluid channel 138 in electrode 88 that is in fluid communication with fluid reservoir 134 and control unit 136.

Figure 29:
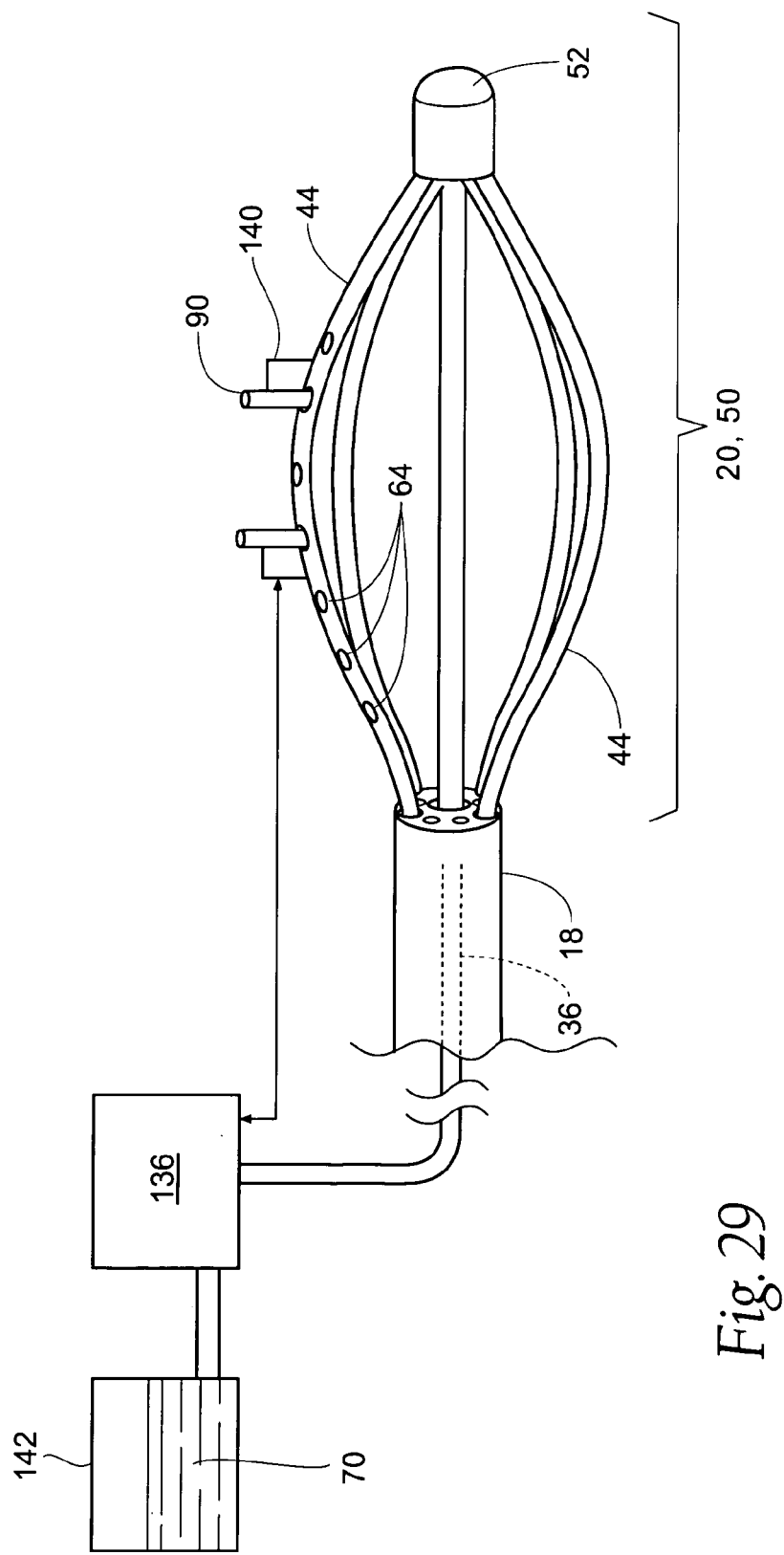
FIG. 29 is an enlarged lateral view illustrating the placement of sensors on the expansion device or basket assembly.

As shown in FIG. 29, one or more sensors 140 may be positioned adjacent to or on electrode 88 for sensing the temperature of sphincter tissue at treatment site 12. More specifically, sensors 140 permit accurate determination of the surface temperature of sphincter wall 26 at electrode-tissue interface 130. This information can be used to regulate both the delivery of energy and cooling solution 70 to the interior surface of sphincter wall 26. In various embodiments, sensors 140 can be positioned at any position on expandable mapping assembly 20 or basket assembly 50. Suitable sensors that may be used for sensor 140 include: thermocouples, fiber optics, resistive wires, thermocouple IR detectors, and the like. Suitable thermocouples for sensor 140 include: T type with copper constantene, J type, E type and K types as are well known those skilled in the art.

Temperature data from sensors 140 are fed back to control unit 136 and through an algorithm which is stored within a microprocessor memory of control unit 136. Instructions are sent to an electronically controlled micropump (not shown) to deliver fluid through the fluid lines at the appropriate flow rate and duration to provide control temperature at the electrode-tissue interface 130 (refer to FIG. 27).

The reservoir of control unit 136 may have the ability to control the temperature of the cooling solution 70 by either cooling the fluid or heating the fluid. Alternatively, a fluid reservoir 134 of sufficient size may be used in which the cooling solution 70 is introduced at a temperature at or near that of the normal body temperature. Using a thermally insulated reservoir 142, adequate control of the tissue temperature may be accomplished without need of refrigeration or heating of the cooling solution 70. Cooling solution 70 flow is controlled by control unit 136 or another feedback control system (described herein) to provide temperature control at the electrode-tissue interface 130.

A second diagnostic phase may be included after the treatment is completed. This provides an indication of LES tightening treatment success, and whether or not a second phase of treatment, to all or only a portion of the esophagus, now or at some later time, should be conducted. The second diagnostic phase is accomplished through one or more of the following methods: (i) visualization, (ii) measuring impedance, (iii) ultrasonography, (iv) temperature measurement, or (v) measurement of LES tension and contractile force via manometry.

Figure 30:
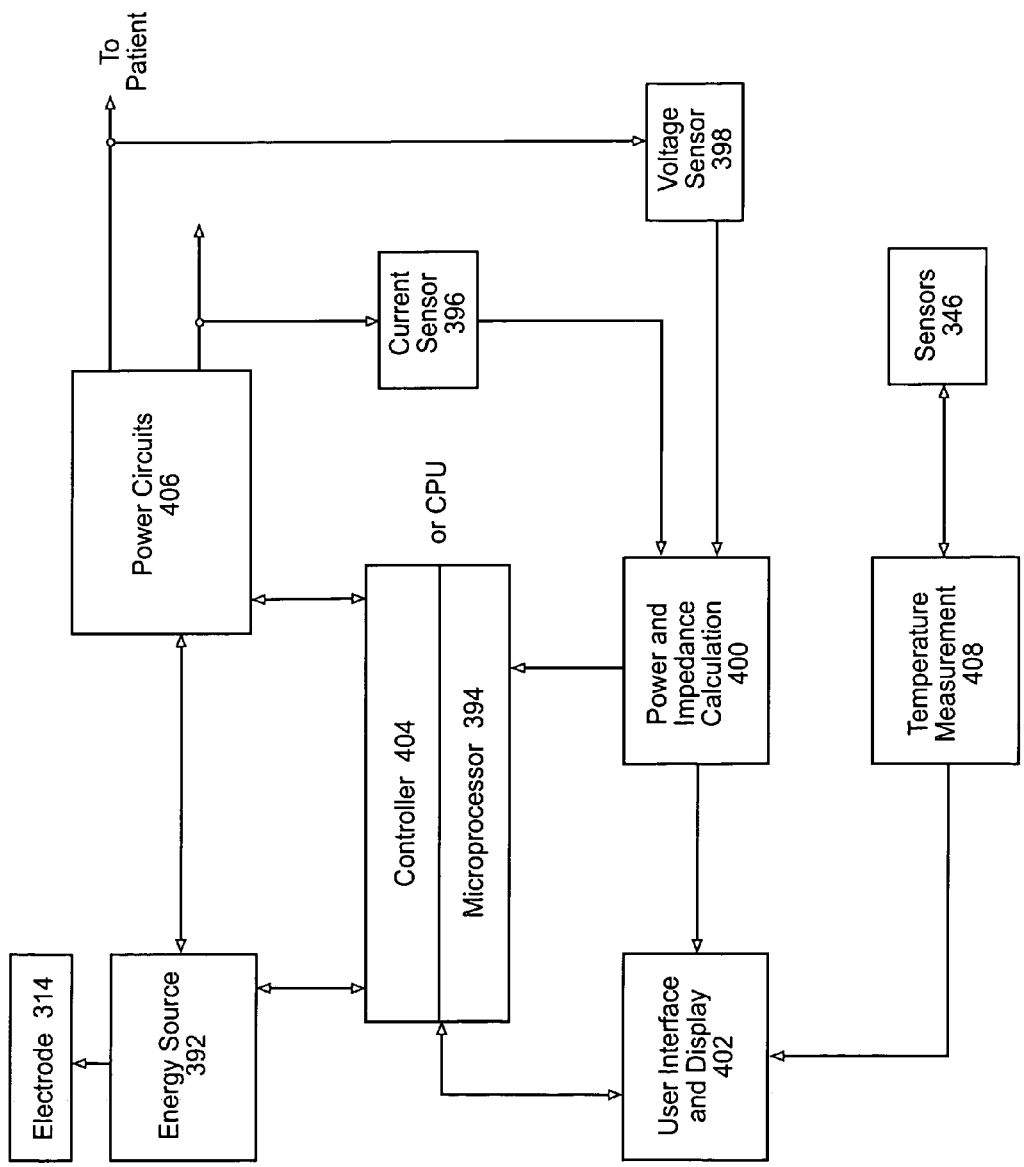
FIG. 30 depicts a block diagram of the feed back control system that can be used with the sphincter mapping and treatment apparatus.

In one embodiment, sphincter mapping and treatment apparatus 10 is coupled to an open or closed loop feedback system. Referring now to FIG. 30, an open or closed loop feedback system couples sensor 346 to energy source 392. In this embodiment, electrode 314 is one or more RF electrodes 314.

The temperature of the tissue, or of RF electrode 314 is monitored, and the output power of energy source 392 adjusted accordingly. The physician can, if desired, override the closed or open loop system. A microprocessor 394 can be included and incorporated in the closed or open loop system to switch power on and off, as well as modulate the power. The closed loop system utilizes microprocessor 394 to serve as a controller, monitor the temperature, adjust the RF power, analyze the result, refeed the result, and then modulate the power.

With the use of sensor 346 and the feedback control system a tissue adjacent to RF electrode 314 can be maintained at a desired temperature for a selected period of time without causing a shut down of the power circuit to electrode 314 due to the development of excessive electrical impedance at electrode 314 or adjacent tissue as is discussed herein. Each RF electrode 314 is connected to resources which generate an independent output. The output maintains a selected energy at RF electrode 314 for a selected length of time.

Current delivered through RF electrode 314 is measured by current sensor 396. Voltage is measured by voltage sensor 398. Impedance and power are then calculated at power and impedance calculation device 400. These values can then be displayed at user interface and display 402. Signals representative of power and impedance values are received by a controller 404.

A control signal is generated by controller 404 that is proportional to the difference between an actual measured value, and a desired value. The control signal is used by power circuits 406 to adjust the power output in an appropriate amount in order to maintain the desired power delivered at respective RF electrodes 314.

In a similar manner, temperatures detected at sensor 346 provide feedback for maintaining a selected power. Temperature at sensor 346 is used as a safety means to interrupt the delivery of energy when maximum pre-set temperatures are exceeded. The actual temperatures are measured at temperature measurement device 408, and the temperatures are displayed at user interface and display 402. A control signal is generated by controller 404 that is proportional to the difference between an actual measured temperature and a desired temperature. The control signal is used by power circuits 406 to adjust the power output in an appropriate amount in order to maintain the desired temperature delivered at the sensor 346. A multiplexer can be included to measure current, voltage and temperature, at the sensor 346, and energy can be delivered to RF electrode 314 in monopolar or bipolar fashion.

Controller 404 can be a digital or analog controller, or a computer with software. When controller 404 is a computer it can include a CPU coupled through a system bus. This system can include a keyboard, a disk drive, or other non-volatile memory systems, a display, and other peripherals, as are known in the art. Also coupled to the bus is a program memory and a data memory.

User interface and display 402 includes operator controls and a display. Controller 404 can be coupled to imaging systems including, but not limited to, ultrasound, CT scanners, X-ray, MRI, mammographic X-ray and the like. Further, direct visualization and tactile imaging can be utilized.

The output of current sensor 396 and voltage sensor 398 are used by controller 404 to maintain a selected power level at RF electrode 314. The amount of RF energy delivered controls the amount of power. A profile of the power delivered to electrode 314 can be incorporated in controller 404 and a preset amount of energy to be delivered may also be profiled.

Circuitry, software and feedback to controller 404 result in process control, the maintenance of the selected power setting which is independent of changes in voltage or current, and is used to change the following process variables: (i) the selected power setting, (ii) the duty cycle (e.g., on-off time), (iii) bipolar or monopolar energy delivery; and, (iv) fluid delivery, including flow rate and pressure. These process variables are controlled and varied, while maintaining the desired delivery of power independent of changes in voltage or current, based on temperatures monitored at sensor 346.

Figure 31:
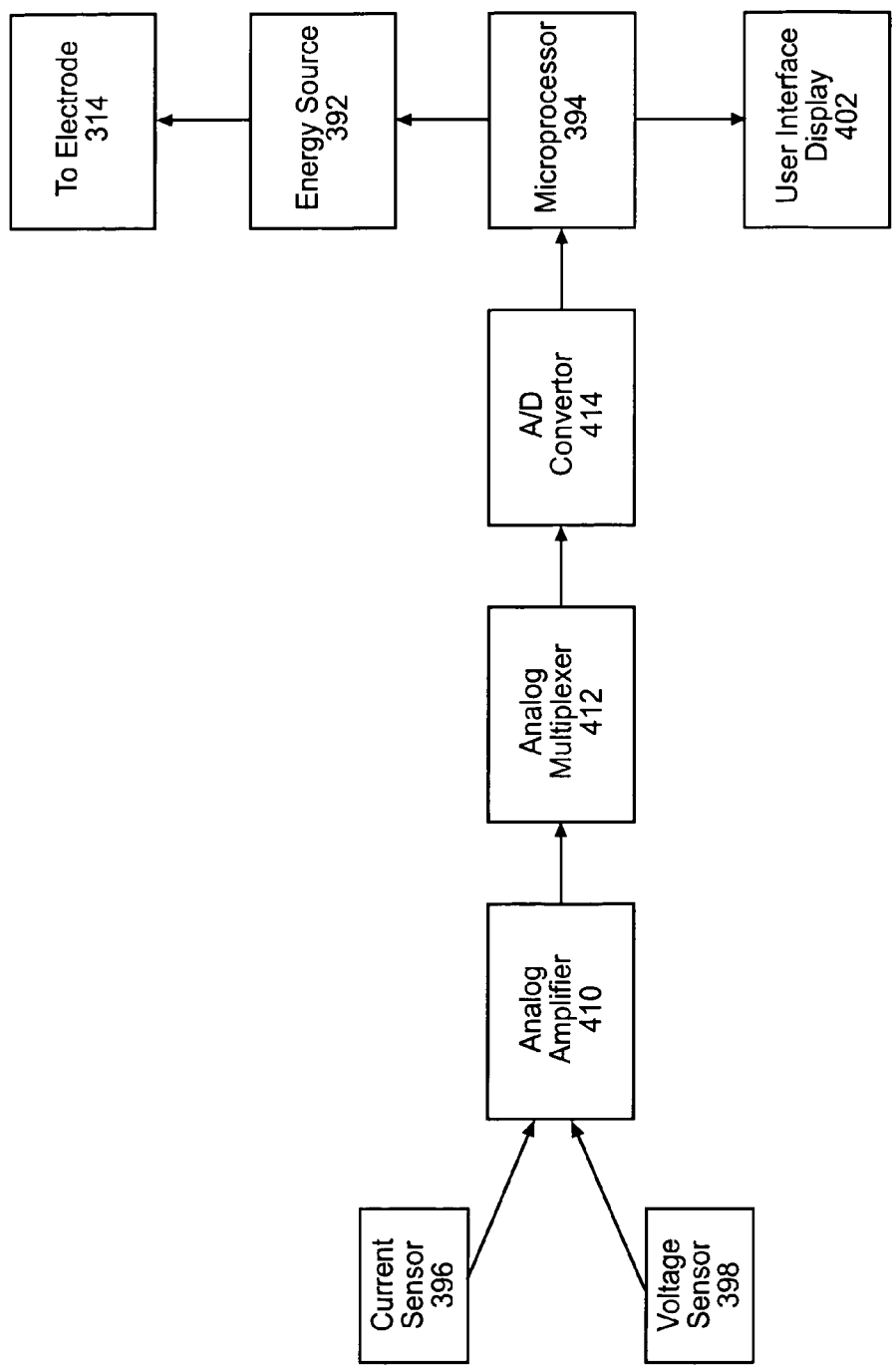
FIG. 31 depicts a block diagram of an analog amplifier, analog multiplexer and microprocessor used with the feedback control system of FIG. 30.

Referring now to FIG. 31, current sensor 396 and voltage sensor 398 are connected to the input of an analog amplifier 410. Analog amplifier 410 can be a conventional differential amplifier circuit for use with sensor 346. The output of analog amplifier 410 is sequentially connected by an analog multiplexer 412 to the input of A/ID converter 414. The output of analog amplifier 410 is a voltage which represents the respective sensed temperatures. Digitized amplifier output voltages are supplied by A/D converter 414 to microprocessor 394. Microprocessor 394 may be a type 68HCII available from Motorola. However, it will be appreciated that any suitable microprocessor or general purpose digital or analog computer can be used to calculate impedance or temperature.

Microprocessor 394 sequentially receives and stores digital representations of impedance and temperature. Each digital value received by microprocessor 394 corresponds to different temperatures and impedances.

Calculated power and impedance values can be indicated on user interface and display 402. Alternatively, or in addition to the numerical indication of power or impedance, calculated impedance and power values can be compared by microprocessor 394 to power and impedance limits. When the values exceed predetermined power or impedance values, a warning can be given on user interface and display 402, and additionally, the delivery of RF energy can be reduced, modified or interrupted. A control signal from microprocessor 394 can modify the power level supplied by energy source 392.

Figure 32:
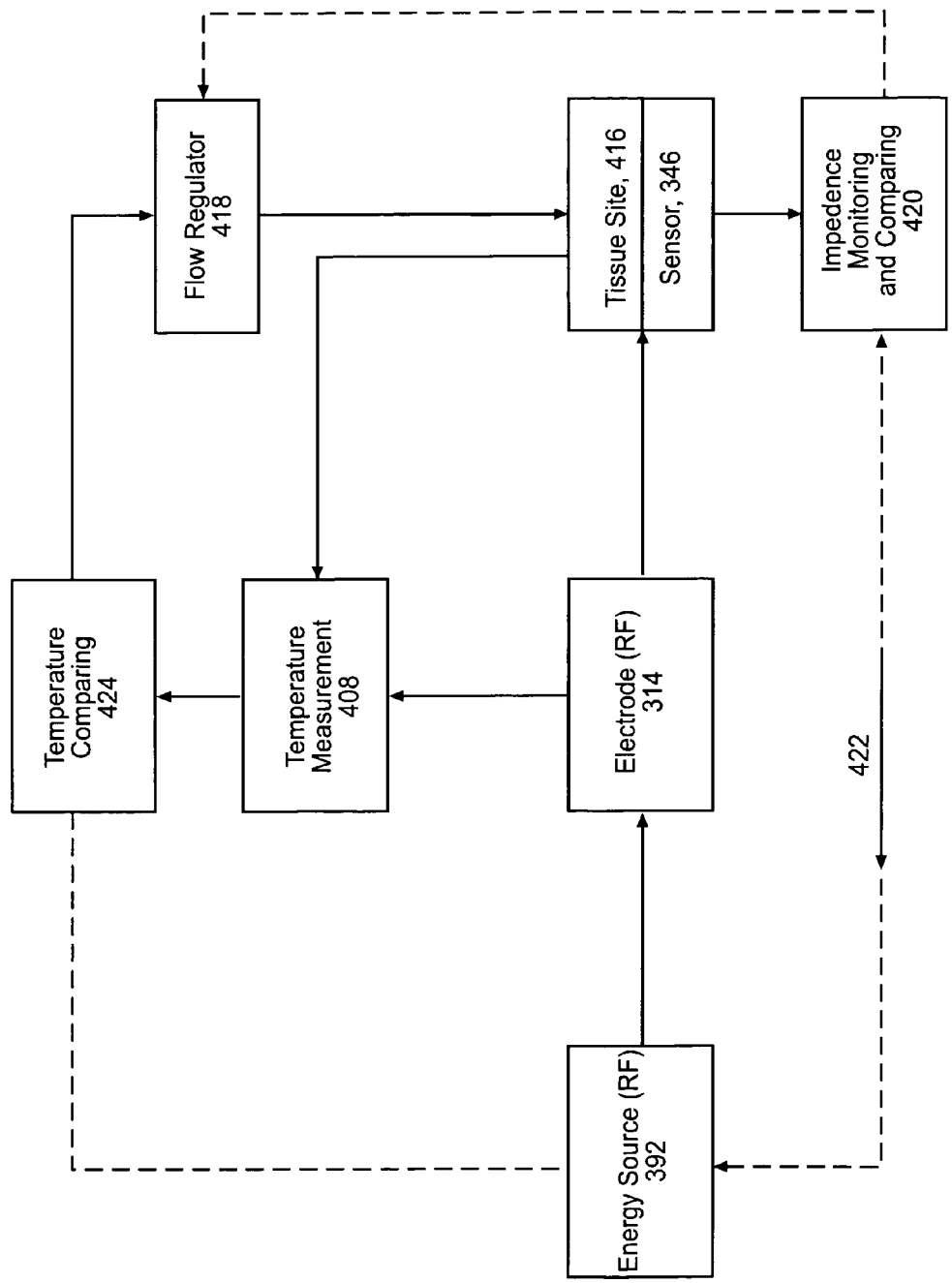
FIG. 32 depicts a block diagram of the operations performed in the feedback control system depicted in FIG. 30.

FIG. 32 illustrates a block diagram of a temperature and impedance feedback system that can be used to control the delivery of energy to tissue site 416 by energy source 392 and the delivery of cooling solution 70 to electrode 314 and/or tissue site 416 by flow regulator 418. Energy is delivered to RF electrode 314 by energy source 392, and applied to tissue site 416. A monitor 420 ascertains tissue impedance, based on the energy delivered to tissue, and compares the measured impedance value to a set value. If the measured impedance exceeds the set value, a disabling signal 422 is transmitted to energy source 392, ceasing further delivery of energy to RF electrode 314. If measured impedance is within acceptable limits, energy continues to be applied to the tissue.

The control of cooling solution 70 to electrode 314 and/or tissue site 416 is done in the following manner. During the application of energy, temperature measurement device 408 measures the temperature of tissue site 416 and/or RF electrode 314. A comparator 424 receives a signal representative of the measured temperature and compares this value to a preset signal representative of the desired temperature. If the tissue temperature is too high, comparator 424 sends a signal to a flow regulator 418 (connected to an electronically controlled micropump, not shown) representing a need for an increased cooling solution flow rate. If the measured temperature has not exceeded the desired temperature, comparator 424 sends a signal to flow regulator 418 to maintain the cooling solution flow rate at its existing level.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method comprising
    deploying a catheter in association with tissue at or near a sphincter, the catheter carrying a mapping device,
    operating the mapping device to detect electrical events in the tissue,
    analyzing the detected electrical events,
    diagnosing dysfunction affecting the tissue based, at least in part, upon the analysis,
    selecting at least one target tissue treatment site based, at least in part, upon the analysis,
    deploying a catheter in association with the at least one target tissue treatment site, the catheter carrying a treating device, and
    operating the treating device to alter the detected electrical events and thereby treat the dysfunction.

2. A method according to claim 1 further comprising, after operating the treating device, repeating an operation of the mapping device to detect electrical events in the tissue, re-analyzing the detected electrical events, and determining whether the dysfunction has been treated based, at least in part, upon the re-analysis.

3. A method according to claim 2 further comprising, after a determination that the dysfunction remains, repeating an operation of the treating device.

4. A method according to claim 1 wherein deploying the catheter in association with tissue at or near a sphincter includes deploying the catheter adjacent tissue in an esophagus.

5. A method according to claim 1 wherein deploying the catheter in association with tissue at or near a sphincter includes deploying the catheter adjacent tissue in a stomach.

6. A method according to claim 1 wherein deploying a catheter in association with tissue at or near a sphincter and deploying a catheter in association with the at least one target tissue treatment site comprising deploying a single catheter carrying both a mapping device and a treating device.

* * * * *